United States Patent
Hölscher

(10) Patent No.: US 11,220,534 B2
(45) Date of Patent: Jan. 11, 2022

(54) TREATMENT OF NEUROLOGICAL DISEASES

(71) Applicant: Lancaster University Business Enterprises Limited, Lancaster (GB)

(72) Inventor: Christian Hölscher, Lancaster (GB)

(73) Assignee: Lancaster University Business Enterprises Limited, Lancaster (GB)

( * ) Notice: Subject to any disclaimer, the term of this patent is extended or adjusted under 35 U.S.C. 154(b) by 97 days.

(21) Appl. No.: 16/466,194

(22) PCT Filed: Dec. 4, 2017

(86) PCT No.: PCT/GB2017/053655
§ 371 (c)(1),
(2) Date: Jun. 3, 2019

(87) PCT Pub. No.: WO2018/104718
PCT Pub. Date: Jun. 14, 2018

(65) Prior Publication Data
US 2020/0079832 A1    Mar. 12, 2020

(30) Foreign Application Priority Data
Dec. 5, 2016  (GB) .................... 1620611

(51) Int. Cl.
| | | |
|---|---|---|
| *A61K 38/00* | (2006.01) | |
| *C07K 14/605* | (2006.01) | |
| *A61K 47/54* | (2017.01) | |
| *A61P 25/28* | (2006.01) | |
| *A61P 25/16* | (2006.01) | |

(52) U.S. Cl.
CPC .......... *C07K 14/605* (2013.01); *A61K 47/542* (2017.08); *A61P 25/16* (2018.01); *A61P 25/28* (2018.01); *A61K 38/00* (2013.01)

(58) Field of Classification Search
CPC ...... C07K 14/605; C07K 14/00; A61K 38/00; A61K 47/542; A61P 25/00; A61P 25/28; A61P 21/00; A61P 25/02; A61P 25/08; A61P 25/14; A61P 25/16; A61P 25/24; A61P 43/00; A61P 9/10
See application file for complete search history.

(56) References Cited

U.S. PATENT DOCUMENTS

| | | |
|---|---|---|
| 9,884,091 B2 | 2/2018 | Holscher |
| 2016/0015788 A1 | 1/2016 | Holscher |
| 2017/0112897 A1 | 4/2017 | Talbot et al. |

FOREIGN PATENT DOCUMENTS

| | | | |
|---|---|---|---|
| GB | 2528436 A | 1/2016 | |
| JP | 2009/523129 A | 6/2009 | |
| JP | 2012/505637 A | 3/2012 | |
| JP | 2014/525430 A | 8/2017 | |
| WO | 2007/081792 A2 | 7/2007 | |
| WO | 2010011439 A2 | 1/2010 | |
| WO | 2010/043047 A1 | 4/2010 | |
| WO | 2011094337 A1 | 8/2011 | |
| WO | 2012050921 A2 | 4/2012 | |
| WO | 2013/030409 A1 | 3/2013 | |
| WO | 2013054110 A2 | 4/2013 | |
| WO | 2013164483 A1 | 11/2013 | |
| WO | 2013192129 A1 | 12/2013 | |
| WO | WO-2013192129 A1 * | 12/2013 | ................ A61P 3/04 |
| WO | 2015/181756 A1 | 12/2015 | |
| WO | 2017075505 A2 | 5/2017 | |
| WO | 2017210168 A1 | 12/2017 | |

OTHER PUBLICATIONS

Thorkildsen et al. 2003. Glucagon-Like Peptide 1 Receptor Agonist ZP10A Increases Insulin mRNA Expression and Prevents Diabetic Progression in db/db Mice. J Pharmacol Exp Ther, 307 (2003), pp. 490-496 (Year: 2003).*
Johns Hopkins medicine Accessed Dec. 23, 2020 at https://www.hopkinsmedicine.org/health/conditions-and-diseases/neurological-disorders (Year: 2020).*
Murphy et al. Alzheimer's Disease and the β-Amyloid Peptide. J Alzheimers Dis. Jan. 2010 ; 19(1): 311 (Year: 2010).*
JPND Research. Accessed Dec. 22, 2020 at https://www.neurodegenerationresearch.eu/what/ (Year: 2019).*
Ji et al. A novel dual GLP-1 and GIP receptor agonist is neuroprotective in the MPTP mouse model of Parkinson's disease by increasing expression. Brain research 1634 (2016) 1-11 (Year: 2015).*
Cedar Sinai. Accessed on Dec. 22, 2020 on https://www.cedars-sinai.org/programs/neurology-neurosurgery/conditions.html (Year: 2020).*
Kiran et al. Mental, Neurological, and Substance Use Disorders: Disease Control Priorities, Third Edition (vol. 4) (Year: 2016).*
Sharifi et al. Treatment of neurological and psychiatric disorders with deep brain stimulation; raising hopes and future challenges. 2013. Basic Clin Neurosci. Summer 2013;4(3):266-70 (Year: 2013).*
Athauda et al. The glucagon-like peptide 1 (GLP) receptor as a therapeutic target in Parkinson's disease: mechanisms of action. Drug Discovery Today vol. 21, Issue 5, May 2016, pp. 802-818 (Year: 2016).*
Aviles-Olmos et al.: "Exenatide and the treatment of patients with Parkinson's disease", The Journal of clinical investigation, 123:2730-6, 2013.

(Continued)

*Primary Examiner* — James H Alstrum-Acevedo
*Assistant Examiner* — Mercy H Sabila
(74) *Attorney, Agent, or Firm* — Dinsmore & Shohl LLP

(57) ABSTRACT

Aspects and embodiments of the present invention relate to the treatment of neurological disorders such as for example, Alzheimer's disease and Parkinson's disease. Particularly, certain embodiments relate to GIP/GLP-1 co-agonist peptides for use in the treatment of these two neurological disorders. Also included in the present invention are inter alia pharmaceutical compositions comprising the GIP/GLP-1 co-agonist peptides, together with methods of treating such disorders as well as other subject matter.

8 Claims, 12 Drawing Sheets

Specification includes a Sequence Listing.

(56) References Cited

OTHER PUBLICATIONS

Aviles-Olmos et al.: "Motor and Cognitive Advantages Persist 12 Months After Exenatide Exposure in Parkinson's Disease", Journal of Parkinson's disease, 4:337-344, 2014.
Baggio et al.: "Biology of incretins: GLP-1 and GIP", Gastroenterology, 132:2131-2157, 2007.
Bertilsson et al.: "Peptide Hormone Exendin-4 Stimulates Subventricular Zone Neurogenesis in the Adult Rodent Brain and Induces Recovery in an Animal Model of Parkinson's Disease", Journal of neuroscience research, 86:326-338, 2008.
Blennow et al.: "Alzheimer's disease", Lancet, 368:387-403, 2006.
Bliss et al.: "A synaptic model of memory: long-term potentiation in the hippocampus", Nature, 361:31-39, 1993.
Bomfim et al.: "An anti-diabetes agent protects the mouse brain from defective insulin signaling caused by Alzheimer's disease-associated Aβ oligomers", The Journal of clinical investigation, 122:1339-53, 2012.
Campbell and Drucker, "Pharmacology, Physiology, and Mechanisms of Incretin Hormone Action", Cell Metabolism, (2013), http://dx.doi.org/10.1016/j.cmet.2013.04.008.
Cao et al.: "A novel dual GLP-1 and GIP incretin receptor agonist is neuroprotective in a mouse model of Parkinson's disease by reducing chronic inflammation in the brain", pp. 384-391, NeuroReport, vol. 27, No. 6, Apr. 2016.
Cereda et al.: "Clinical features of Parkinson disease when onset of diabetes came first: A case-control study", Neurology, 78:1507-1511, 2012.
Christensen et al.: "Lixisenatide, a novel GLP-1 receptor agonist for the treatment of type 2 diabetes mellitus", IDrugs, 2009; 12(8):503-513.
Cleary et al.: "Natural oligomers of the amyloid-beta protein specifically disrupt cognitive function", Nature neuroscience, 8:79-84, 2005.
Duffy et al.: "The incretin analogue D-Ala(2)GIP reduces plaque load, astrogliosis and oxidative stress in an APP/PS1 mouse model of Alzheimer's disease", Neuroscience, 228:294-300, 2013.
Elkinson et al.: "Lixisenatide: first global approval", Drugs, 73:383-391, 2013.
Faivre et al.: "Effects of acute and chronic administration of GIP analogues on cognition, synaptic plasticity and neurogenesis in mice", European Journal of Pharmacology, 674, 294-306, 2012.
Faivre et al.: "D-Ala2GIP Facilitated Synaptic Plasticity and Reduces Plaque Load in Aged Wild Type Mice and in an Alzheimer's Disease Mouse Model", J. Alzheimer's Dis., 35:267-283, 2013.
Faivre et al.: "Glucose-dependent insulinotropic polypeptide receptor knockout mice are impaired in learning, synaptic plasticity, and neurogenesis", J Neurophysiol, 105:1574-1580, 2011.
Faivre et al.: "Neuroprotective effects of D-Ala2GIP on Alzheimer's disease biomarkers in an APP/PS1 mouse model", Alzheimer's research & therapy, 5:20-28, 2013.
Gault et al.: "GLP-1 agonists facilitate hippocampal LTP and reverse the impairment of LTP induced by beta-amyloid", European journal of pharmacology, 587:112-117, 2008.
Gault et al.: "Glucose-dependent insulinotropic polypeptide (GIP): anti-diabetic and anti-obesity potential?", Neuropeptides, 37, 253-263, 2003.
Gault et al.: "Glucose-dependent insulinotropic polypeptide analogues and their therapeutic potential for the treatment of obesity-diabetes", Biochemical and biophysical research communications, 308:207-213, 2003.
Gault et al.: "Protease-resistant glucose-dependent insulinotropic polypeptide agonists facilitate hippocampal LTP and reverse the impairment of LTP induced by beta-amyloid", J Neurophysiol, 99:1590-1595, 2008.
Gegl et al.: "In Alzheimer's Disease, Six-Month Treatment with GLP-1 Analogue Prevents Decline of Brain Glucose Metabolism: Randomized, Placebo-Controlled, Double-Blind Clinical Trial", Frontiers in aging neuroscience, 8; Article 108: pp. 1-10, 2016.
Gengler et al.: "Val(8)GLP-1 rescues synaptic plasticity and reduces dense core plaques in APP/PS1 mice", Neurobiology of aging, 33:265-276, 2010.
Han et al.: Neuroprotective effect of hydroxysafflor yellow A on 6-hydroxydopamine-induced Parkinson's disease in rats, European journal of pharmacology, 714:83-88, 2013.
Harkavyi et al.: "Glucagon-like peptide 1 receptor stimulation reverses key deficits in distinct rodent models of Parkinson's disease", Journal of Neuroinflammation, 2008, 5:19 doi:10.1186/1742-2094-5-19.
Holscher: "Insulin, incretins and other growth factors as potential novel treatments for Alzheimer's and Parkinson's diseases", Biochemical Society transactions, 42: (2014) 1-7; doi:10.1042/BST20140016.
Hunter et al.: "Drugs developed to treat diabetes, liraglutide and lixisenatide, cross the blood brain barrier and enhance neurogenesis", BMC neuroscience, 13:33-38, 2012.
Irwin et al.: "GIP(Lys(16)PAL) and GIP(Lys(37)PAL): Novel Long-Acting Acylated Analogues of Glucose-Dependent Insulinotropic Polypeptide with Improved Antidiabetic Potential", Journal of medicinal chemistry, 49:1047-1054, 2006.
Ji et al.: "A novel dual GLP-1 and GIP receptor agonist is neuroprotective in the MPTP mouse model of Parkinson's disease by increasing expression of BNDF", pp. 1-11, Brain Research, vol. 1634, Mar. 2016.
Kristensen et al.: "Applications and challenges for use of cell-penetrating peptides as delivery vectors for peptide and protein cargos", p. E185, International Journal of Molecular Sciences, vol. 17, No. 2, Jan. 2016.
LaFerla et al.: "Alzheimer's disease: Abeta, tau and synaptic dysfunction", Trends Mol Med, 11:170-176, 2005.
Li et al.: "GLP-1 receptor stimulation preserves primary cortical and dopaminergic neurons in cellular and rodent models of stroke and Parkinsonism", Proceedings of the National Academy of Sciences of the United States of America, 106:1285-1290, 2009.
Li et al.: "Neuroprotective effects of a GIP analogue in the MPTP Parkinson's disease mouse model", Neuropharmacology, 101:255-263, 2016.
Liu et al.: "Neuroprotective effects of lixisenatide and liraglutide in the MPTP mouse model of Parkinson's disease", Neuroscience, 303:42-50, 2015.
Liu et al.: "Polymeric micelles anchored with TAT for delivery of antibiotics across the blood-brain barrier", Biopolymers, 90:617-623, 2008.
Lovshin et al.: "Incretin-based therapies for type 2 diabetes mellitus", Nature reviews Endocrinology, 5:262-269, 2009.
Luchsinger et al.: "Hyperinsulinemia and risk of Alzheimer disease", Neurology, 63:1187-1192, 2004.
McClean et al.: "Glucagon-like peptide-1 analogues enhance synaptic plasticity in the brain: A link between diabetes and Alzheimer's disease", European journal of pharmacology, 630:158-162, 2010.
McClean et al.: "Liraglutide can reverse memory impairment, synaptic loss and reduce plaque load in aged APP/PS1 mice, a model of Alzheimer's disease", Neuropharmacol, 76:57-67, 2014.
McClean et al.: "The Diabetes Drug Liraglutide Prevents Degenerative Processes in a Mouse Model of Alzheimer's Disease", Journal of neuroscience, 31:6587-6594, 2011.
Moloney et al.: "Defects in IGF-1 receptor, insulin receptor and IRS-1/2 in Alzheimer's disease indicate possible resistance to IGF-1 and insulin signalling", Neurobiology of Aging, 31:224-243, 2010.
Morris et al.: "Insulin resistance impairs nigrostriatal dopamine function", Experimental neurology, 231:171-180, 2011.
Nyberg et al.: "Immunohistochemical Distribution of Glucose-Dependent Insulinotropic Polypeptide in the Adult Rat Brain", Journal of neuroscience research, 85:2099-2119, 2007.
Ohara et al.: "Glucose tolerance status and risk of dementia in the community: The Hisayama Study", Neurology, 77:1126-1134, 2011.
Parthsarathy et al.: "A novel retro-inverso peptide inhibitor reduces amyloid deposition, oxidation and inflammation and stimulates neurogenisis in the APPswe/PSIDeltaE9 mouse model of Alzheimer's disease", p. e54769, Plos One, vol. 8, No. 1, 2013.

(56) References Cited

OTHER PUBLICATIONS

Radde et al.: "Abeta42-driven cerebral amyloidosis in transgenic mice reveals early and robust pathology", EMBO Reports, 7:940-946, 2006.
Ristow: "Neurodegenerative disorders associated with diabetes mellitus", J Mol Med, 82:510-529, 2004.
Scherrmann: "Drug delivery to brain via the blood-brain barrier", Vascul Pharmacol, 38:349-354, 2002.
Shen: "Impaired neurotransmitter release in Alzheimer's and Parkinson's diseases", Neuro-degenerative diseases, 7:80-83, 2010.
Talbot et al.: "Demonstrated brain insulin resistance in Alzheimer's disease patients is associated with IGF-1 resistance, IRS-1 dysregulation, and cognitive decline", The Journal of clinical investigation, 122:1316-38, 2012.
Verspohl : "Novel therapeutics for type 2 diabetes: Incretin hormone mimetics (glucagon-like peptide-1 receptor agonists) and dipeptidyl peptidase-4 inhibitors", pp. 113-138, Pharmacology & Therapeutics, vol. 124, No. 1, Oct. 2009.
Windisch et al.: Neurotrophic activities and therapeutic experience with a brain derived peptide preparation, Journal of neural transmission, Supplement, 53: 289-298, 1998.
Orlando, M., "Modification of Proteins and Low Molecular Weight Substances with Hydroxyethyl Starch (HES)" Inaugurald Dissertation, Giessen, 2003.
Arnau, J. et al., Protein Expression and Purification, 48(1): 1-13, 2006.
Chen, X. et al., Advanced Drug Delivery Reviews, 65(10): 1357-1369, 2013.
Maeda, Y. et al., Analytical Biochemistry, 249(2): 147-152, 1997.
Muller, S. et al., Arthritis & Rheumatism: Official Journal of the American College of Rheumatology, 58(12): 3873-3883, 2008.
Office Action in corresponding Russia Patent Application No. 2019118165 dated Mar. 5, 2021.
Arnau, J. et al., "Current strategies for the use of affinity tags and tag removal for the purification of recombinant proteins." Protein Expression and Purification, 48(1): 1-13, 2006.
Chen, X. et al., "Fusion protein linkers: property, design and functionality." Advanced Drug Delivery Reviews, 65(10): 1357-1369, 2013.
Maeda, Y. et al., "Engineering of functional chimeric protein G—Vargula Luciferase." Analytical Biochemistry, 249(2): 147-152, 1997.
Muller, S. et al., "Spliceosomal peptide P140 for immunotherapy of systemic lupus erythematosus: results of an early phase II clinical trial." Arthritis & Rheumatism: Official Journal of the American College of Rheumatology, 58(12): 3873-3883, 2008.

* cited by examiner

Figure 12

Tyr-Aib-Glu-Gly-Thr-Phe-Thr-Ser-Asp-Tyr-Ser-Ile-Tyr-Leu-Asp-Lys-Gln-Ala-Ala-Aib-Glu-Phe-Val-Xaa$^{24}$-Trp-Leu-Leu-Ala-Gly-Y1-Y2-R$^2$
SEQ. ID. No 1

Lys-Lys-Lys-Lys-Lys (SEQ. ID. No 2);

Lys-Lys-Lys-Lys-Lys-Lys (SEQ. ID. No. 3)

Arg-Arg-Gln-Arg-Arg-Lys-Lys-Arg-Gly-Tyr (SEQ. ID. No 4); and

Lys-Arg-Arg-Gln-Arg-Arg-Lys-Lys-Arg-Gly-Tyr (SEQ. ID. No 5);

Gly-Pro-Ser-Ser-Gly-Ala-Pro-Pro-Pro-Ser (SEQ. ID. No. 6);
Gly-Pro-Ser-Ser-Gly-Ala-Pro-Pro-Pro-Ser-Lys (SEQ. ID. No. 7);
Gly-Pro-Ser-Ser-Gly-Ala-Pro-Pro-Pro-Ser-Cys (SEQ. ID. No. 8);
Pro-Ser-Ser-Gly-Ala-Pro-Pro-Pro-Ser (SEQ. ID. No. 9);
Pro-Ser-Ser-Gly-Ala-Pro-Pro-Ser (SEQ. ID. No. 10);

YXEGTFTSDYSIYLDKQAAXEFVNWLLAGGPSSGAPPPSKKKKKK-NH2
SEQ ID No 11
YXEGTFTSDYSIYLDKQAAXEFVNWLLAGGPSSGAPPPSKRRQRRKKRGY-NH2
X = aminoisobutyric acid
SEQ. ID. No 12

HAEGTFTSDV SSYLEGQAAK EFIAWLVKGR G-OH (SEQ ID No. 13)

YAEGTFISDYSIAMDKIHQQDFVNWLLAQKGKKNDWKHNITQ-OH (SEQ ID. No 14)

His Ala Glu Gly Thr Phe Thr Ser Asp Val Ser Ser Tyr Leu Glu Gly Gln Ala Ala Xaa Glu Phe Ile Ala Trp Leu Val Arg Gly Arg (SEQ ID No. 15)

Y$d$-AEGTFISDYSIAMDKIHQQDFVNWLLAQKGKK(γ-E-C16)NDWKHNITQ (SEQ ID. No 16)

TREATMENT OF NEUROLOGICAL DISEASES

TECHNICAL FIELD OF THE INVENTION

Aspects and embodiments of the present invention relate to the treatment of neurological disorders such as for example, Alzheimer's disease and Parkinson's disease. Particularly, certain embodiments relate to GIP/GLP-1 co-agonist peptides for use in the treatment of these two neurological disorders. Also included in the present invention are inter alia pharmaceutical compositions comprising the GIP/GLP-1 co-agonist peptides, together with methods of treating such disorders as well as other subject matter.

BACKGROUND TO THE INVENTION

Alzheimer's disease (AD) is a chronic neurodegenerative disorder for which there is at present no cure. Currently prescribed medication only temporarily relieves some of the symptoms. The main hallmarks of the disease are disorientation, loss of memory, loss of neurons and synapses in the brain, the accumulation of beta-amyloid protein in the brain (amyloid plaques), and intracellular aggregation of hyperphosphorylated tau protein (tangles) (LaFerla and Oddo, 2005; Blennow et al., 2006).

Parkinson's disease (PD) is also a chronic neurodegenerative disease for which currently only delaying medication is available. The main hallmarks are tremor, rigor, and a loss of ability to move, the degeneration of neurons in the basal brain (substantia nigra) and the loss of release of the neurotransmitter, dopamine (Shen, 2010).

Type 2 diabetes (T2DM) has been identified as a risk factor for AD and PD (Holscher, 2014), indicating that insulin signalling impairment may be a factor in initiating or accelerating the development of AD. Epidemiological studies found a clear correlation between T2DM and the risk of developing AD or other neurodegenerative disorders at a later stage (Luchsinger et al., 2004; Ristow, 2004; Ohara et al., 2011). It was also shown that insulin signalling in the brain is desensitized in AD patients. Recent studies demonstrated that brains of AD patients had increased levels of inactivated phosphorylated insulin receptors and IRS-1 second messengers, which are both indicative of insulin desensitization (Moloney et al., 2010; Bomfim et al., 2012; Talbot et al., 2012). In PD, insulin signalling was also found to be impaired and linked to disease progression (Morris et al., 2011; Cereda et al., 2012). Glucagon-like peptide (GLP-1) is an endogenous 30-amino acid peptide incretin hormone (Baggio and Drucker, 2007). GLP-1 receptor stimulation enhances beta-cell proliferation in the pancreas by activating stem cell proliferation, facilitates glucose-dependent insulin secretion and lowers blood glucose in patients with T2DM (Lovshin and Drucker, 2009). Three GLP-1 analogues are currently on the market as a treatment for diabetes, exendin-4 (Byetta®, Bydureon®), lixisenatide (Lyxumia®) and liraglutide (Victoza®) (Campbell and Drucker, 2013; Elkinson and Keating, 2013).

Glucose-dependent insulinotropic peptide (GIP), also known as gastric inhibitory polypeptide, is a 42-amino acid incretin hormone which activates pancreatic islets to enhance insulin secretion and to help reduce postprandial hyperglycaemia, similar to GLP-1 (Gault et al., 2003). GIP is a member of the secretin/glucagon family of neuroregulatory polypeptides which also include the growth hormone releasing factor. It is expressed in pancreatic alpha cells, endocrine cells, and also in neurons in the brain (Nyberg et al., 2007; Campbell and Drucker, 2013). GIP has also been shown to promote pancreatic beta-cell growth, differentiation, proliferation and cell survival, documenting its growth-hormone properties (Gault et al., 2003). Therefore, research is on-going to develop GIP as a therapeutic tool for T2DM treatment (Irwin et al., 2006). There are currently no GIP analogues authorised for the treatment of T2DM.

Dual agonist peptides which target more than one receptor are being considered for the treatment of T2DM. Several GIP/GLP-1 co-agonist peptides are currently in development for the treatment of T2D. However, there are currently no GIP/GLP-1 dual receptor agonists authorised for use to treat T2DM.

Recent investigations of the neuroproperties of GLP-1 and GIP have indicated that these peptides may play a role in preventing neurodegenerative hallmarks in several mouse models of Alzheimer's disease (AD) and also in animal models of Parkinson's disease (PD).

Insulin as well as the incretins not only have growth-factor like properties in the brain, but also modulate synaptic activity (Holscher, 2014). Synapses are the contacts between neurons, and they are important for memory formation and information processing in the brain. Direct injection of GLP-1 or long-lasting GLP-1 analogues into the brain markedly enhanced long-term potentiation of synaptic transmission (LTP) in the hippocampus, a brain area that is involved in memory formation. LTP is considered a cellular correlate of memory formation (Bliss and Collingridge, 1993). The GLP-1 analogue, liraglutide, has been shown to upregulate LTP in the rat brain (McClean et al., 2010).

In addition, GLP-1 analogues were able to prevent the impairment of LTP that was induced by beta-amyloid fragments (Gault and Holscher, 2008a; McClean et al., 2011; Gengler et al., 2012; Han et al., 2013). This impairment of LTP by amyloid protein may be the mechanism by which amyloid causes memory loss (Cleary et al., 2005). A study testing liraglutide in an APP/PS1 mouse model of AD showed that the drug can prevent the impairment in memory formation and synaptic plasticity, the reduction of total numbers of synapses, normalise stem cell proliferation and neurogenesis in the dentate gyrus, reduce the inflammation response, and furthermore reduce amyloid plaque load in the cortex and total amyloid levels in the brain (McClean et al., 2011). In another study, liraglutide also had protective and regenerative effects in very old transgenic mice, demonstrating that even at an advanced stage of disease progression, memory can be improved and plaque load be reduced to some degree (McClean and Holscher, 2014).

Based on these findings in animal models, a pilot clinical trial in Alzheimer's patients has been conducted. The finding was that the GLP-1 analogue liraglutide protected the disease-induced degeneration of brain activity and energy utilization. This demonstrates that the drug enters the brain and protects neurons from the damaging effects of Alzheimer's while keeping neurons active and functional (Gejl et al., 2016). A phase II clinical trial of liraglutide in AD patients has started (NCT01843075).

Furthermore, one prior art study has investigated the effects of the GLP-1 receptor agonist exendin-4 in the 6-hydroxydopamine model of PD. After the lesion was induced, rats were treated with exendin-4 and a protection of motor activity was observed. Histological analysis showed that exendin-4 significantly increased the number of both tyrosine hydroxylase- and vesicular monoamine transporter 2-positive neurons in the substantia nigra (Bertilsson et al., 2008). In a second study, two rodent models of PD, 6-hydroxydopamine (6-OHDA) and lipopolysaccharide (LPS), were used to test the effects of exendin-4. Motor control was much improved in the drug group, and striatal tissue concentrations of dopamine were markedly higher. In addition, exendin-4 reversed the loss of extracellular DA in the striatum (Harkavyi et al., 2008). When testing the GLP-1 receptor agonists liraglutide and lixisenatide in the MPTP mouse model of Parkinson's disease, it was found that both drugs showed good effects in preventing the motor impairment, chronic inflammation in the brain, and loss of dopaminergic neurons induced by the toxin MPTP (Liu et al., 2015).

Based on these studies, a clinical trial of exendin-4 in PD patients had been initiated. This study reported that in several motor assessments and in a cognitive test, patients had improved, and the improvements were maintained even after the drug had been discontinued for 12 months (Aviles-Olmos et al., 2013; Aviles-Olmos et al., 2014). A phase II clinical trial in Parkinson's patients testing the drug liraglutide has started (NCT02953665).

Studies have also been carried out to determine whether GIP or GIP analogues have an effect in AD. It has been found that GIP analogues can prevent the LTP impairment that beta-amyloid fragments induce on synaptic transmission in the brain (Gault and Holscher, 2008b). In a GIP receptor-deletion mouse strain, LTP was also impaired, and paired-pulse facilitation was reduced, indicating that the release of synaptic vesicles is reduced (Faivre et al., 2011). The long-lasting GIP analogue D-Ala$^2$-GIP also had neuroprotective effects in an APP/PS1 mouse model of AD. In 12 months old mice, synaptic plasticity in area CA1 of the hippocampus and spatial memory formation was impaired in APP/PS1 mice but was unimpaired in D-Ala$^2$-GIP treated APP/PS1 mice. In addition, the amyloid plaque load was much reduced, showing impressive effects in reducing the main hallmarks of AD (Faivre and Holscher, 2013b).

In aged 19 month old AD mice, the drug was still able to reverse some of the AD symptoms such as synapse loss (Faivre and Holscher, 2013a). In a longitudinal study, oxidative stress and the inflammation response in the brain was much reduced in APP/PS1 mice (Duffy and Holscher, 2013). This suggests that these analogues have neuroprotective properties in AD and protect synapses from the detrimental effects of beta-amyloid.

In the MPTP mouse model of Parkinson's disease, the GIP analogue D-Ala$^2$-GIP was protective and prevented the impairment of motor activity, the loss of dopaminergic neurons, loss of synapses and the chronic inflammation response induced by MPTP (Li et al., 2015). When testing a novel dual GLP-1/GIP dual agonist in this mouse model, it was found that it showed good protective effects (Ji et al., 2015). However, that particular molecule was not as effective as GLP-1 analogues.

There remains a need to identify treatments for neurological disorders such as for example the neurodegenerative diseases, Alzheimer's disease and Parkinson's disease.

It is an aim of certain embodiments of the present invention to at least partly mitigate the problems associated with the prior art.

It is an aim of certain embodiments of the present invention to provide a therapeutic peptide for use in the treatment and/or prevention of a neurodegenerative disorder such as for example Alzheimer's disease and/or Parkinson's disease.

It is an aim of certain embodiments of the present invention to provide novel GIP/GLP-1 dual agonist peptides which have superior efficacy as compared to the best in class GLP-1 mono agonist liraglutide, for use in the treatment and/or prevention of Alzheimer's or Parkinson's disease.

It is an aim of certain embodiments of the present invention to provide GIP/GLP-1 dual agonist peptides which have superior properties as compared to a GIP mono agonist. Examples of superior properties include for example a greater decrease in beta-amyloid plaque load and/or reduction of motor skill impairment.

It is an aim of certain embodiments of the present invention to provide novel GIP/GLP-1 dual agonist peptides for use in the treatment and/or prevention of a neurodegenerative disorder such as for example Alzheimer's disease and/or Parkinson's disease.

SUMMARY OF THE INVENTION

In one aspect of the present invention, there is provided a GIP/GLP-1 co-agonist peptide or a pharmaceutically acceptable salt or solvate thereof for use in the treatment and/or prophylaxis of a neurological disorder, wherein the co-agonist peptide is represented by the general formula 1:

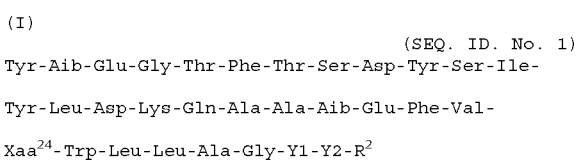

wherein Xaa$^{24}$ is selected from Asn and Cys;
Y1 is selected from absent or an extension comprising at least eight amino acid molecules;
Y2 is selected from:

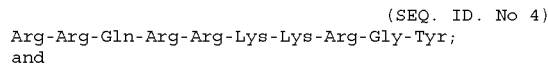

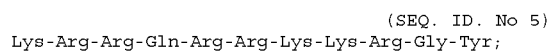

R$^2$ is selected from —NH2 or —OH, or a derivative or a pharmaceutically acceptable salt or solvate of the peptide or the derivative.

In certain embodiments, Y2 is Lys-Lys-Lys-Lys-Lys or Lys-Lys-Lys-Lys-Lys-Lys.

In certain embodiments, Y2 is Arg-Arg-Gln-Arg-Arg-Lys-Lys-Arg-Gly-Tyr or Lys-Arg-Arg-Gln-Arg-Arg-Lys-Lys-Arg-Gly-Tyr.

In certain embodiments, Xaa$^{24}$ is Cys. In certain embodiments, Xaa$^{24}$ is Asn.

In certain embodiments, Y1 is an extension comprising at least 10 amino acids e.g. at least 11 amino acids.

In certain embodiments, Y1 is selected from:

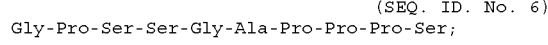

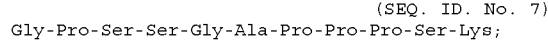

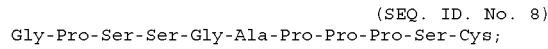

```
                                      (SEQ. ID. No. 9)
    Pro-Ser-Ser-Gly-Ala-Pro-Pro-Pro-Ser;

(SEQ. ID. No. 10)
    Pro-Ser-Ser-Gly-Ala-Pro-Pro-Ser;
``` and absent.

Aptly, Y1 is Gly-Pro-Ser-Ser-Gly-Ala-Pro-Pro-Pro-Ser (SEQ. ID. No. 6). In certain embodiments, Y1 is Gly-Pro-Ser-Ser-Gly-Ala-Pro-Pro-Pro-Ser-Cys (SEQ. ID. No 8). In an alternative embodiment, Y1 is Gly-Pro-Ser-Ser-Gly-Ala-Pro-Pro-Pro-Ser-Lys (SEQ. ID. No. 7).

In certain embodiments, the peptide comprises a hydrophilic moiety covalently linked to an amino acid. In certain embodiments, the peptide comprises a hydrophilic moiety covalently linked to an amino acid at position 24.

In certain embodiments, the peptide comprises a hydrophilic moiety covalently linked to an amino acid at position 39 or 40, when Y1 is an extension comprising at least 10 amino acids or at least 11 amino acids.

In certain embodiments, Xaa$^{39}$ or Xaa$^{40}$ is Cys and the peptide comprises a hydrophilic moiety covalently linked to Cys(39) or Cys(40).

In certain embodiments, Xaa$^{24}$ is Cys and the peptide comprises a hydrophilic moiety covalently linked to Cys (24).

In certain embodiments, the hydrophilic moiety is a water-soluble polymer.

In certain embodiments, the water-soluble polymer is a polyethylene glycol moiety and optionally is a polyethylene glycol moiety having a molecular weight of between about 20,000 Daltons and about 60,000 Daltons. In certain embodiments, the peptide is conjugated with a lipophilic substituent.

In certain embodiments, the lipophilic substituent comprises a hydrocarbon chain having 8 to 24 carbon (C) atoms. In certain embodiments, the lipophilic substituent comprises an acyl group.

In certain embodiments, the lipophilic substituent is a fatty acid molecule. Aptly, the fatty acid molecule is selected from a C-8 octanoyl group, a C-10 decanoyl group, a C-12 lauroyl group, a C-14 myristoyl group, a C-16 palmitoyl group, a C-18 stearoyl group and a C-20 acyl group.

In certain embodiments, the lipophilic substituent is attached to an amino acid at the carboxyl-terminus of the peptide. In certain embodiments, the lipophilic substituent is attached to an amino acid at position 40. Aptly, the lipophilic substituent is covalently bonded to a side chain of an amino acid of the peptide.

In certain embodiments, the peptide comprises a spacer which conjugates the lipophilic substituent to an amino acid residue. Aptly, the spacer is a residue from a naturally occurring or unnatural amino acid, wherein the spacer comprises a residue of Gly, Pro, Ala, Val, Leu, Ile, Met, Cys, Phe, Tyr, Trp, His, Lys, Arg, Gin, Asn, α-Glu, γ-Glu, ε-Lys, Asp, Ser, Thr, Gaba, Aib, β-aminohexonyl, 7-aminoheptanoyl, 8-aminooctanoyl, 9-aminononanoyl, 10-aminodecanoyl or 8-amino-3,6-dioxaoctanoyl.

In certain embodiments, the spacer is γ-Glu. In certain embodiments, the spacer is a dipeptide, optionally wherein the spacer comprises two negatively charged amino acids and further optionally wherein the spacer is γ-Glu-γ-Glu.

In certain embodiments, the peptide further comprises one or more conservative substitutions.

In certain embodiments, the peptide comprises the amino acid sequence of:

```
                                      (SEQ. ID. No. 11)
    YXEGTFTSDYSIYLDKQAAXEFVNWLLAGGPSSGAPPPSKKKKKK-NH2
``` wherein X=aminoisobutyric acid.

In certain embodiments, the peptide consists essentially of the amino acid sequence of:

```
                                      (SEQ. ID. No. 11)
    YXEGTFTSDYSIYLDKQAAXEFVNWLLAGGPSSGAPPPSKKKKKK-NH2
``` wherein X=aminoisobutyric acid.

In certain embodiments, the peptide comprises the amino acid sequence of:

```
                                      (SEQ. ID. No. 12)
    YXEGTFTSDYSIYLDKQAAXEFVNWLLAGGPSSGAPPPSKRRQRRKKRG
    Y-NH2
``` wherein X=aminoisobutyric acid.

Aptly, the peptide consists essentially of the amino acid sequence of:

```
                                      (SEQ. ID. No. 12)
    YXEGTFTSDYSIYLDKQAAXEFVNWLLAGGPSSGAPPPSKRRQRRKKRG
    Y-NH2
``` wherein X=aminoisobutyric acid.

In a further aspect of the present invention, there is provided a peptide as described herein for use in the treatment and/or prophylaxis of a neurological disorder.

In a further aspect of the present invention, there is provided a peptide as described herein for use in the treatment of a neurological disorder which is caused by or associated with beta-amyloid protein plaque deposition in an area of the patient. In certain embodiments, the beta-amyloid plaque deposition is in the brain of the patient.

In a further aspect of the present invention, there is provided a peptide as described herein for use in the treatment and/or prophylaxis of a neurological disorder caused by, or associated with, dysfunction of long-term potentiation of synaptic transmission.

In a further aspect of the present invention, there is provided a peptide as described herein is for use in the treatment and/or prophylaxis of a neurological disorder caused by, or associated with, inflammation.

In a further aspect of the present invention, there is provided a peptide as described herein for use in the treatment of a neurological disorder associated with motor impairment.

In a further aspect of the present invention, there is provided a peptide as described herein for use in the treatment and/or prophylaxis of a neurological disorder affecting cognitive function, e.g. dementia, stroke, schizophrenia and/or bipolar disorder.

In certain embodiments, the disorder is cerebral ischemia associated with stroke.

In certain embodiments, the peptide is for use in the treatment and/or prophylaxis of a disorder selected from post-traumatic stress disorder, epilepsy, Tourette's syndrome, and hallucinations; and dysfunctional cognitive processes, optionally selected from attention, calculation, memory, judgment, insight, learning and reasoning.

In certain embodiments, the peptide is for use in the treatment and/or prophylaxis of a neurodegenerative disorder e.g. Alzheimer's disease, Parkinson's disease, Amyotrophic Lateral Sclerosis, peripheral neuropathy, Huntington's disease and Creutzfeldt-Jacob disease.

Aptly, the neurological disorder is multiple sclerosis.

In certain embodiments, the peptide is for use in the treatment and/or prophylaxis of a neurological disorder selected from clinical or pre-clinical Alzheimer's disease, prodromal Alzheimer's disease, and clinical or preclinical amyloid angiopathy (CAA).

Aptly, the peptide is for use in the treatment and/or prophylaxis of clinical Alzheimer's disease.

In a further aspect of the present invention, there is provided a peptide as described herein for use in the treatment and/or prophylaxis of Parkinson's disease.

Also provided is a method of treating and/or preventing a neurological disorder as described herein, the method comprising administering a pharmaceutically effective amount of a GIP/GLP-1 co-agonist peptide as described herein to a subject in need thereof.

In a further aspect of the present invention, there is provided a method of treating and/or preventing a neurological disorder comprising administering to a patient in need thereof a pharmaceutical composition comprising a GIP/GLP-1 co-agonist peptide, or a derivative or a pharmaceutically acceptable salt or solvate of the peptide or the derivative, wherein said co-agonist peptide is represented by the general Formula I:

(I)
(SEQ. ID. No. 1)
Tyr-Aib-Glu-Gly-Thr-Phe-Thr-Ser-Asp-Tyr-Ser-Ile-

Tyr-Leu-Asp-Lys-Gln-Ala-Ala-Aib-Glu-Phe-Val-Xaa$^{24}$-

Trp-Leu-Leu-Ala-Gly-Y1-Y2-R2 wherein Xaa$^{24}$ is selected from Asn and Cys;
Y1 is selected from absent or an extension comprising at least eight amino acid molecules;
Y2 is selected from:

(SEQ. ID. No 2)
Lys-Lys-Lys-Lys-Lys;

(SEQ. ID. No. 3)
Lys-Lys-Lys-Lys-Lys-Lys (SEQ. ID. No 4)
Arg-Arg-Gln-Arg-Arg-Lys-Lys-Arg-Gly-Tyr;
and (SEQ. ID. No 5)
Lys-Arg-Arg-Gln-Arg-Arg-Lys-Lys-Arg-Gly-Tyr;

R² is selected from —NH2 or —OH, or a derivative or a pharmaceutically acceptable salt or solvate of the peptide or the derivative.

Aptly, the peptide is as described herein.

In certain embodiments, the neurological disorder is selected from post-traumatic stress disorder, epilepsy, Tourette's syndrome, and hallucinations; and dysfunctional cognitive processes, optionally selected from attention, calculation, memory, judgment, insight, learning and reasoning.

In certain embodiments, the neurological disorder is a neurodegenerative disorder. Aptly, the neurodegenerative disorder is selected from Alzheimer's Disease, Parkinson's Disease, Huntington's disease, Amyotrophic Lateral Sclerosis, peripheral neuropathy, and Creutzfeldt-Jacob disease.

In certain embodiments, the neurological disorder is a neurological disorder selected from clinical or pre-clinical Alzheimer's disease, prodromal Alzheimer's disease, and clinical or preclinical amyloid angiopathy (CAA). APTLY, the neurological disorder is clinical Alzheimer's Disease.

In a further aspect of the present invention, there is provided a peptide for use in the treatment and/or prophylaxis of clinical Alzheimer's Disease, the peptide consisting of the following sequence:

(SEQ. ID. No. 11)
YXEGTFTSDYSIYLDKQAAXEFVNWLLAGGPSSGAPPPSKKKKKK-NH2 wherein X=aminoisobutyric acid.

In a further aspect of the present invention, there is provided a peptide for use in the treatment and/or prophylaxis of clinical Alzheimer's Disease, the peptide consisting of the following sequence:

(SEQ. ID. No. 12)
YXEGTFTSDYSIYLDKQAAXEFVNWLLAGGPSSGAPPPSKRRQRRKKR

GY-NH2 wherein X=aminoisobutyric acid.

In one embodiment, the peptide comprises or consists of the following amino acid sequence:

(SEQ. ID. No. 11)
YXEGTFTSDYSIYLDKQAAXEFVNWLLAGGPSSGAPPPSKKKKKK-NH2

X=aminoisobutyric acid

This peptide is referred to herein as "DA4" and has an amino acid sequence as set forth in SEQ. ID. No. 11.

In one embodiment, the peptide comprises or consists of the following amino acid sequence:

(SEQ. ID. No. 12)
YXEGTFTSDYSIYLDKQAAXEFVNWLLAGGPSSGAPPPSKRRQRRKKR

GY-NH2

X=aminoisobutyric acid

This peptide is referred to herein as "DA5" and has an amino acid sequence as set forth in SEQ. ID. No. 12.

The ability to cross the blood-brain barrier may have utility in the treatment of neurodegenerative disorders. Without being bound by theory, it is considered that the peptides of certain embodiments of the present invention are able to cross the blood-brain barrier. Furthermore, the peptides of certain embodiments cross the blood-brain barrier at an enhanced rate as compared to known GIP/GLP-1 co-agonist peptides.

It is noted that there can be many difficulties in transmission of a peptide across the blood brain barrier. A number of different mechanisms for enhancing access across the blood-brain barrier have been considered, one of which is the modification of peptide sequences. However, whilst a number of peptide modifications are known to potentially assist in crossing the blood-brain barrier, their in vivo behaviour is difficult to predict. Their addition to a peptide or protein molecule may be ineffective or lead to inactivation of the peptide or protein e.g. by protein degradation processes, incorrect peptide folding patterns and/or a change in receptor binding properties of the peptide.

Aptly, the peptide is for use in the treatment and/or prevention of Alzheimer's disease or Parkinson's disease.

Also provided herein is a pharmaceutical composition which comprises GIP/GLP-1 receptor co-agonist peptides as described herein and a pharmaceutically acceptable carrier for use in the treatment and/or prophylaxis of a neurological disorder as described herein. Further provided in the present disclosure is a kit including such a pharmaceutical composition.

BRIEF DESCRIPTION OF DRAWINGS

Further details of embodiments of the invention, with reference to the accompanying drawings by way of example only, are provided below:

As used herein, the abbreviation "DA4" refers to a GIP/GLP-1 co-agonist consisting of the amino acid sequence shown in SEQ ID. No. 11.

As used herein, the abbreviation "DA5" refers to a GIP/GLP-1 co-agonist consisting of the amino acid sequence shown in SEQ ID. No. 12.

Figure 1:
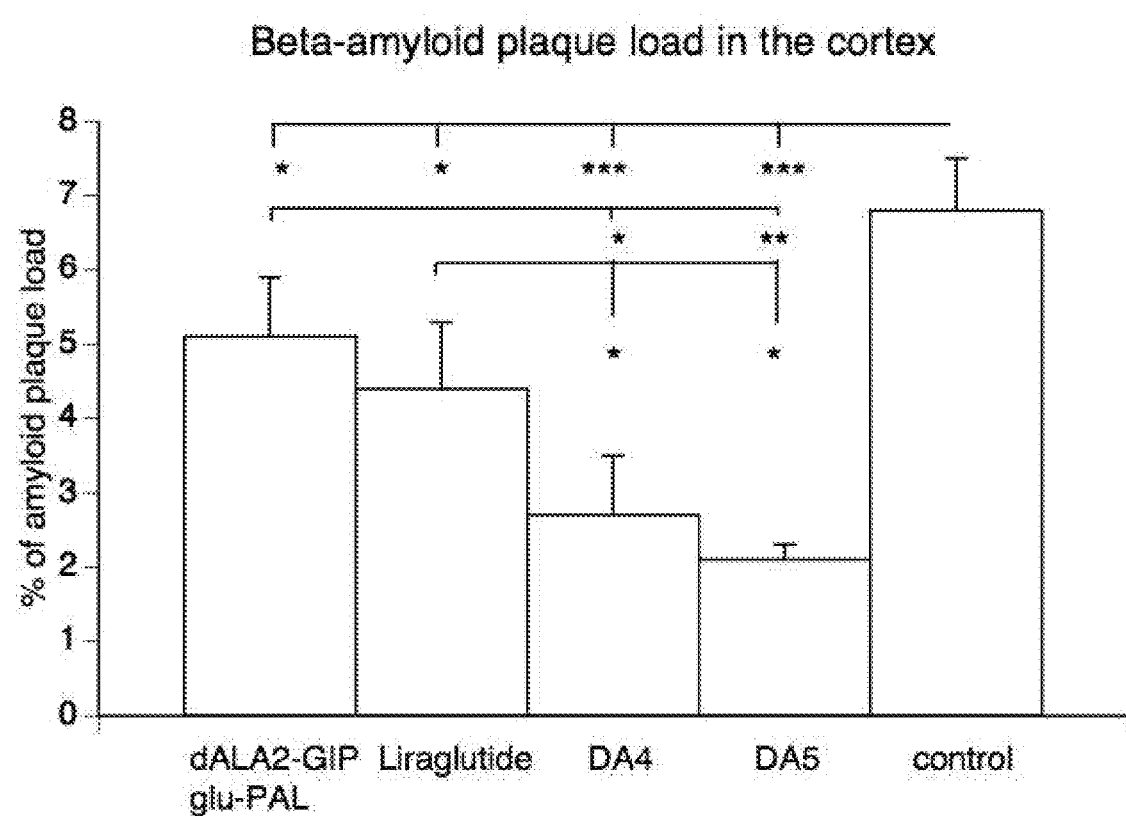

FIG. 1 illustrates an immunohistochemical measurement of beta-amyloid plaque load in the cortex of transgenic mice (Alzheimer's disease model). All peptides reduced the plaque load. Both co-agonist peptides (DA4 and DA5) of embodiments of the present invention were superior to the single GIP or GLP-1 analogues and administration of DA4 and DA5 reduces beta-amyloid plaque load as quantified by beta amyloid immunohistochemistry and determination of the % area positive for beta amyloid in cross sections of the brain cortex. *=p<0.05, =p<0.01; *=p<0.001. N=6 per group.

Figure 2:
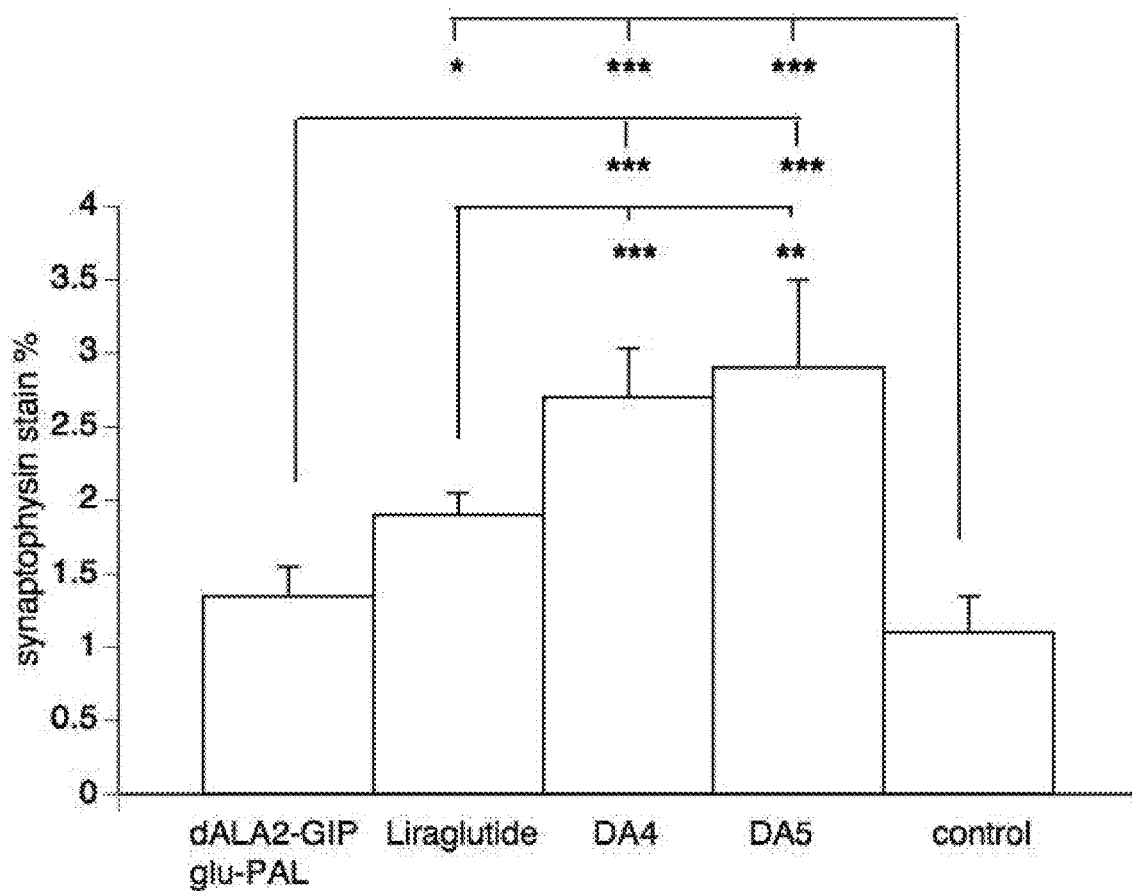

FIG. 2 is a graph illustrating that the DA4 and DA5 peptides protected from synapse loss in the cortex of transgenic mice (Alzheimer's disease model) as quantified by immunohistochemical measurement of synaptic densities in the cortex of the transgenic mice. All peptides protected from synapse loss. Both co-agonist peptides of embodiments of the present invention were superior to the single GIP or GLP-1 analogues. *=p<0.05, =p<0.01; *=p<0.001. N=6 per group.

Figure 3:
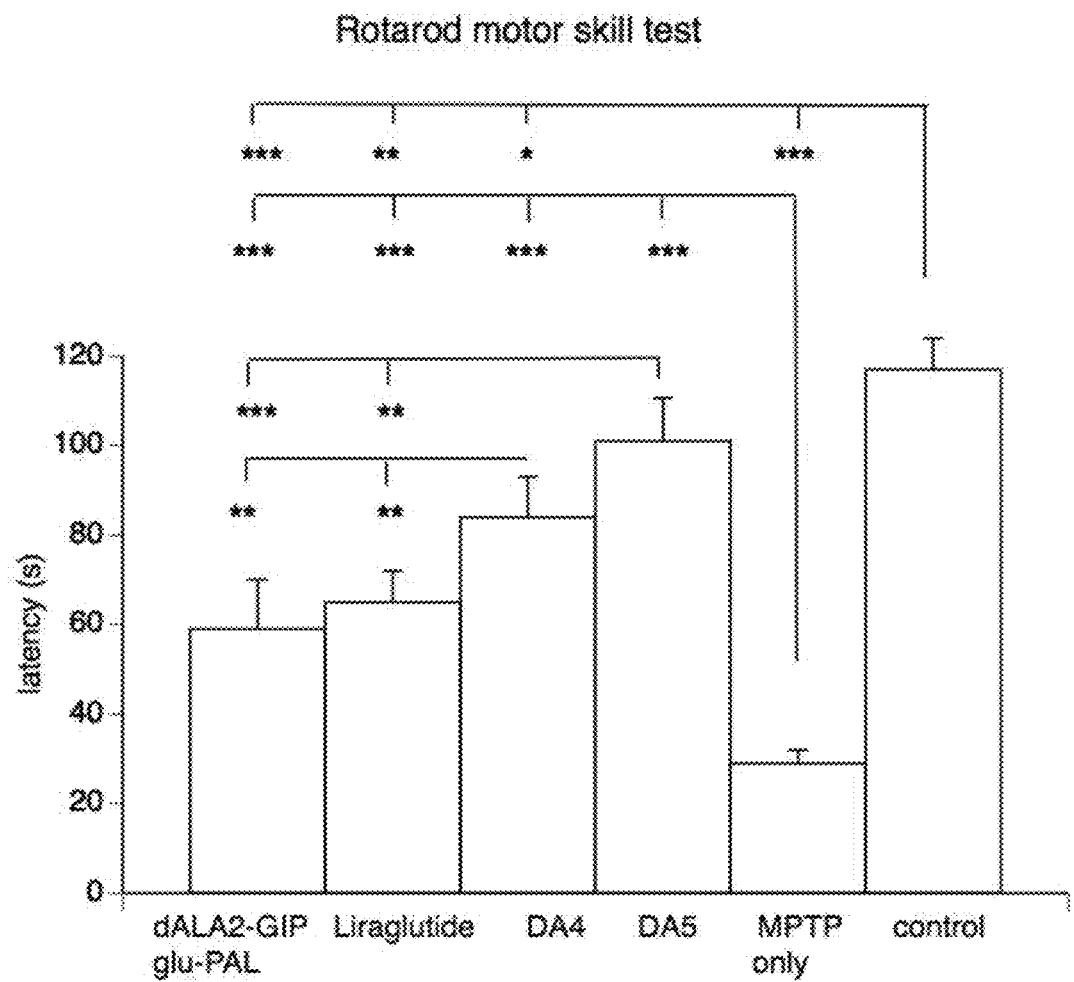

FIG. 3 is a graph illustrating that the DA4 and DA5 peptides protect mice from an impairment of motor skills induced by MPTP to reduce the levels of dopamine. A rotarod motor skill test was carried out as described below. Each animal's endurance time was recorded, and the average was calculated. Data were analysed using a one-way ANOVA with post-hoc Bonferroni tests. Both co-agonist peptides of embodiments of the present invention were superior to the single GIP or GLP-1 analogues. Control=wild type mouse without MPTP. *=p<0.05, =p<0.01; *=p<0.001. N=6 per group.

Figure 4:
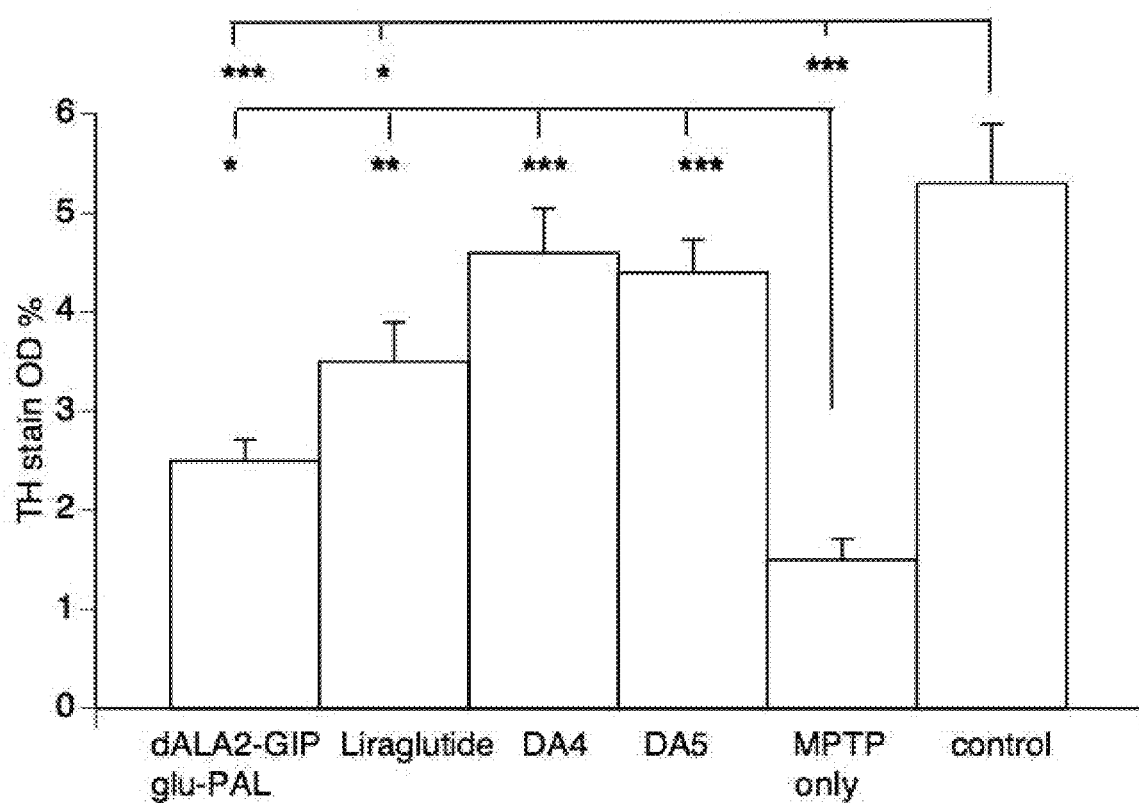

FIG. 4 illustrates MPTP-induced reduction of the enzyme TH that synthetises dopamine in the substantia nigra, pars compacta. Both DA4 and DA5 protected dopaminergic neurons at a greater rate than the single GIP and GLP-1 analogues. *=p<0.05, =p<0.01; *=p<0.001. N=6 per group.

Figure 5:
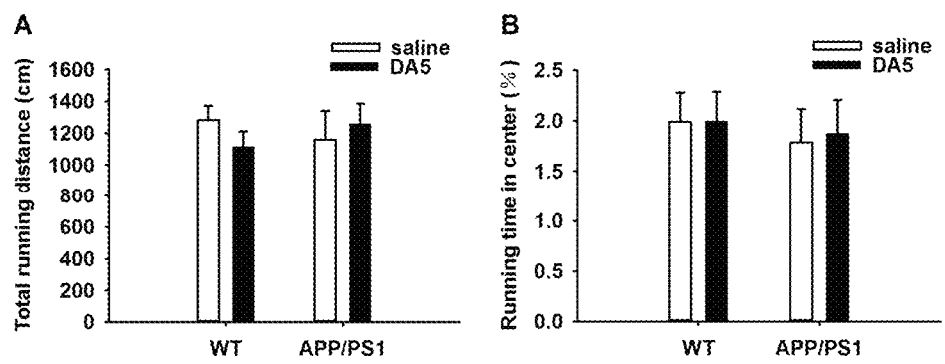

FIG. 5 illustrates that the DA5 peptide does not affect the locomotor and exploratory performance of APP/PS1 and Wild Type mice. An open field test was carried out to measure the spontaneous behaviour of saline/DA5 treated mice. Statistical analysis (p=>0.05) did not show any difference between saline/DA5 groups (a,b).

Figure 6:
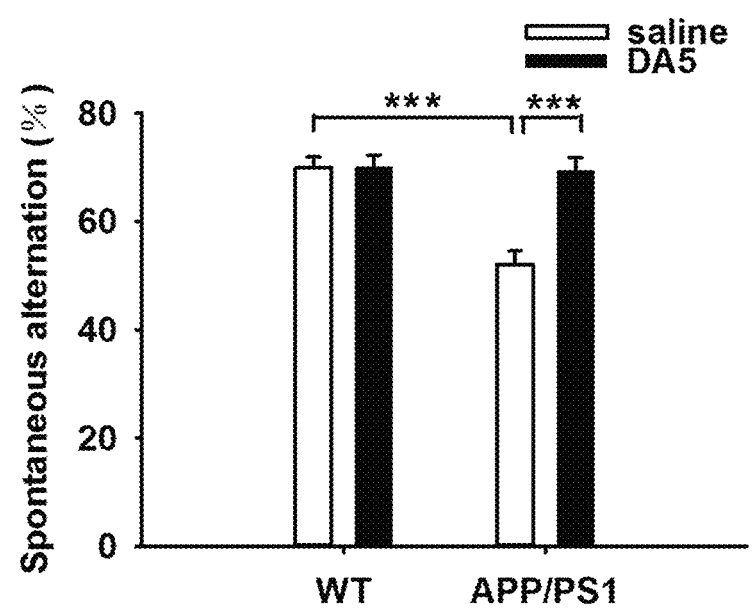

FIG. 6 illustrates improved spatial working memory of APP/PS1 mice in a Y-maze test upon DA5 peptide treatment. The percentage of right alternation in the mice of APP/PS1 mice was significantly reduced. *=p<0.05, =p<0.01; *=p<0.001. N=8-14 per group.

Figure 7:
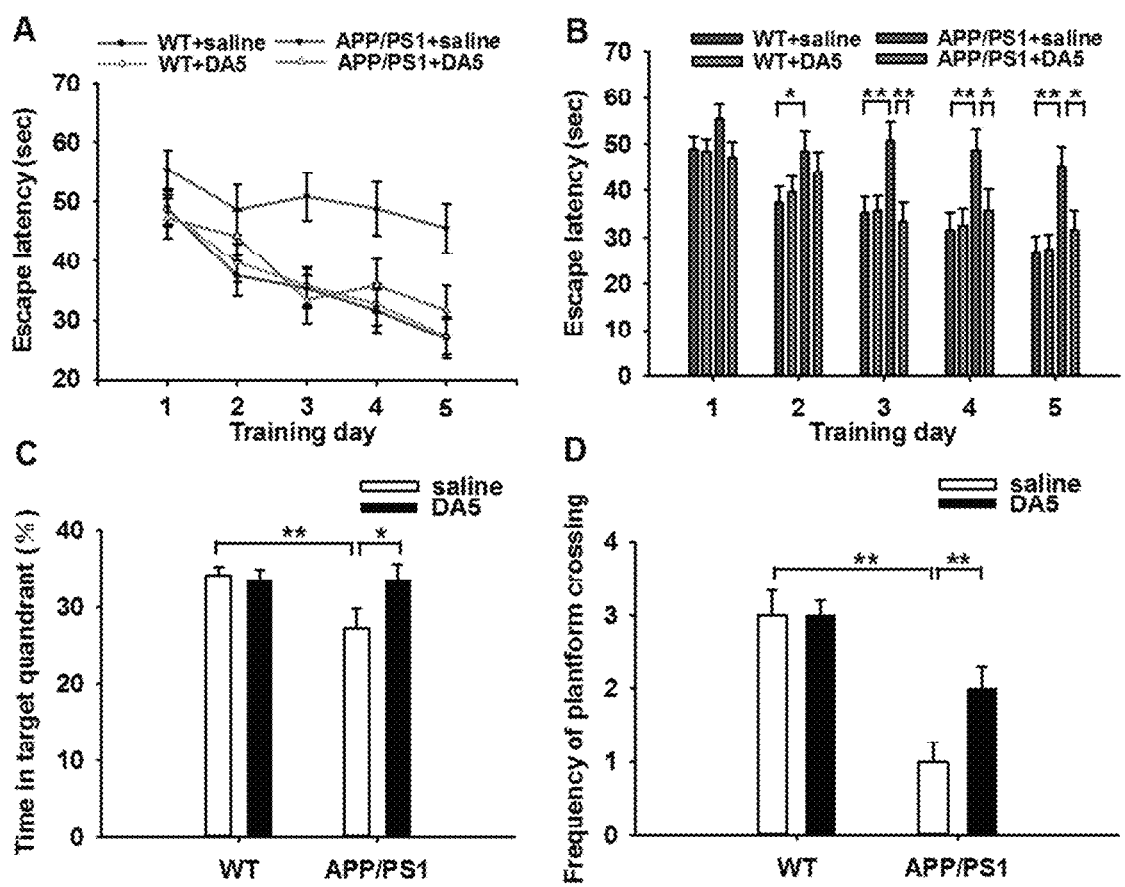

FIG. 7 illustrates the disorder in spatial memory observed in APP/PS1 mice can be ameliorated with DA5 peptide treatment. A classical Morris water maze was carried out and the spatial memory of mice was assessed by a probe trial, as described below. (FIG. 7a, 7b) Each animal's escape latency was recorded over a training period and the average was calculated. (FIG. 7c, 7d). Probe test indicated the DA5 treated APP/PS1 mice recalled the escape route to a greater extent than APP/PS1-saline mice. *=p<0.05, =p<0.01; *=p<0.001. N=8-14 per group.

Figure 8:
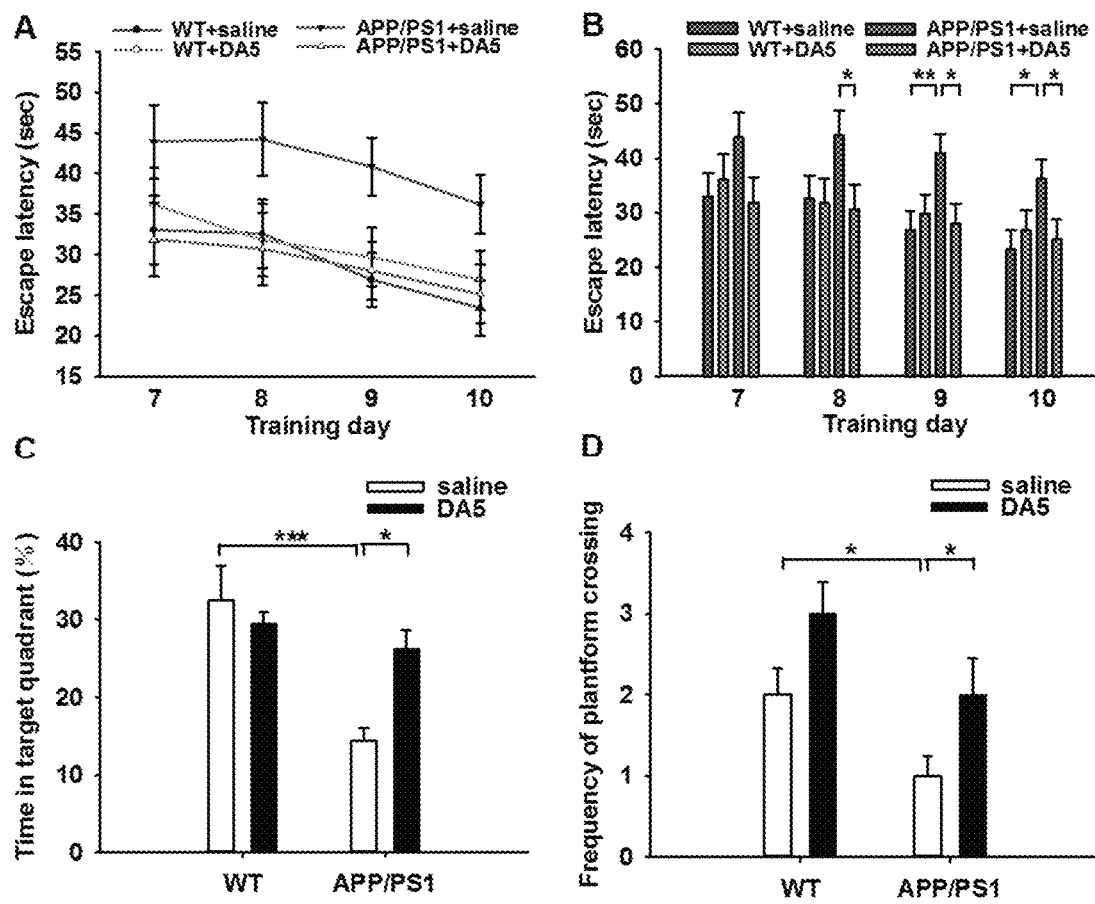

FIG. 8 illustrates that DA5 peptide protects APP/PS1 mice from decreased cognitive flexibility and restores their ability to relearn. A reverse Morris water maze test was carried out as described below. (FIG. 8a, FIG. 8b). Each animal's escape latency was recorded over an extended training period and the average was calculated (FIG. 8c, 8d). Probe test indicated the DA5 treated APP/PS1 mice recalled a change in escape route to a greater extent than APP/PS1-saline mice. *=p<0.05, =p<0.01; *=p<0.001. N=8-14 per group.

Figure 9:
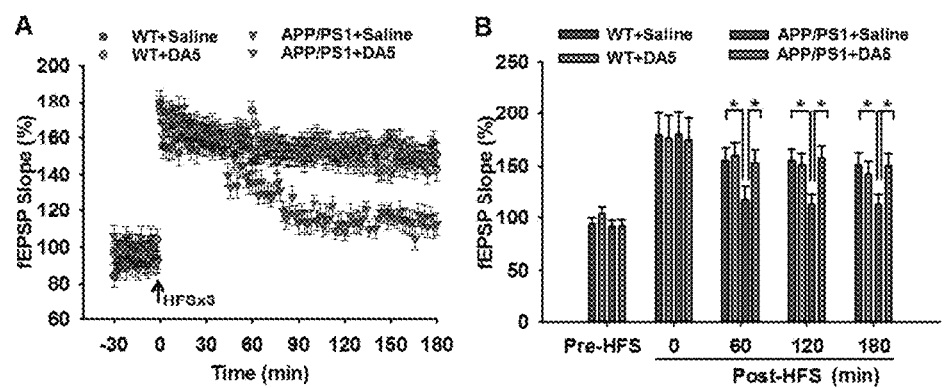

FIG. 9 illustrates that the DA5 peptide maintains synaptic strength in APP/PS1 mice (FIG. 9a) Pre-treatment of mice with DA5 was able to reverse the depression of L-LTP observed in APP/PS1 transgenic mice (FIG. 9b) Furthermore, DA5 treated APP/PS1 mice maintained high levels of L-LTP post neuronal stimuli. *=p<0.05, =p<0.01; *=p<0.001. N=6 per group.

Figure 10:
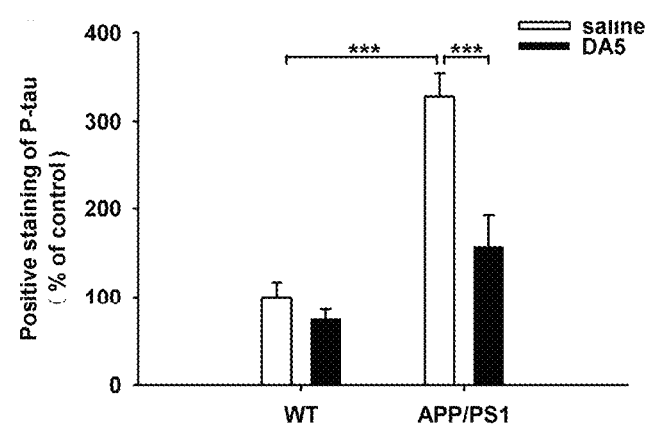

FIG. 10 is a graph illustrating DA5 reduces neurofibrillary tangles in APP/PS1 mice. Quantification of immunofluorescence staining of p-tau protein indicated reduced neurofibrillary tangles in APP/PS1 DA5 treated mice compared to APP/PS1-saline. *=p<0.05, =p<0.01; *=p<0.001. N=4 per group.

Figure 11:
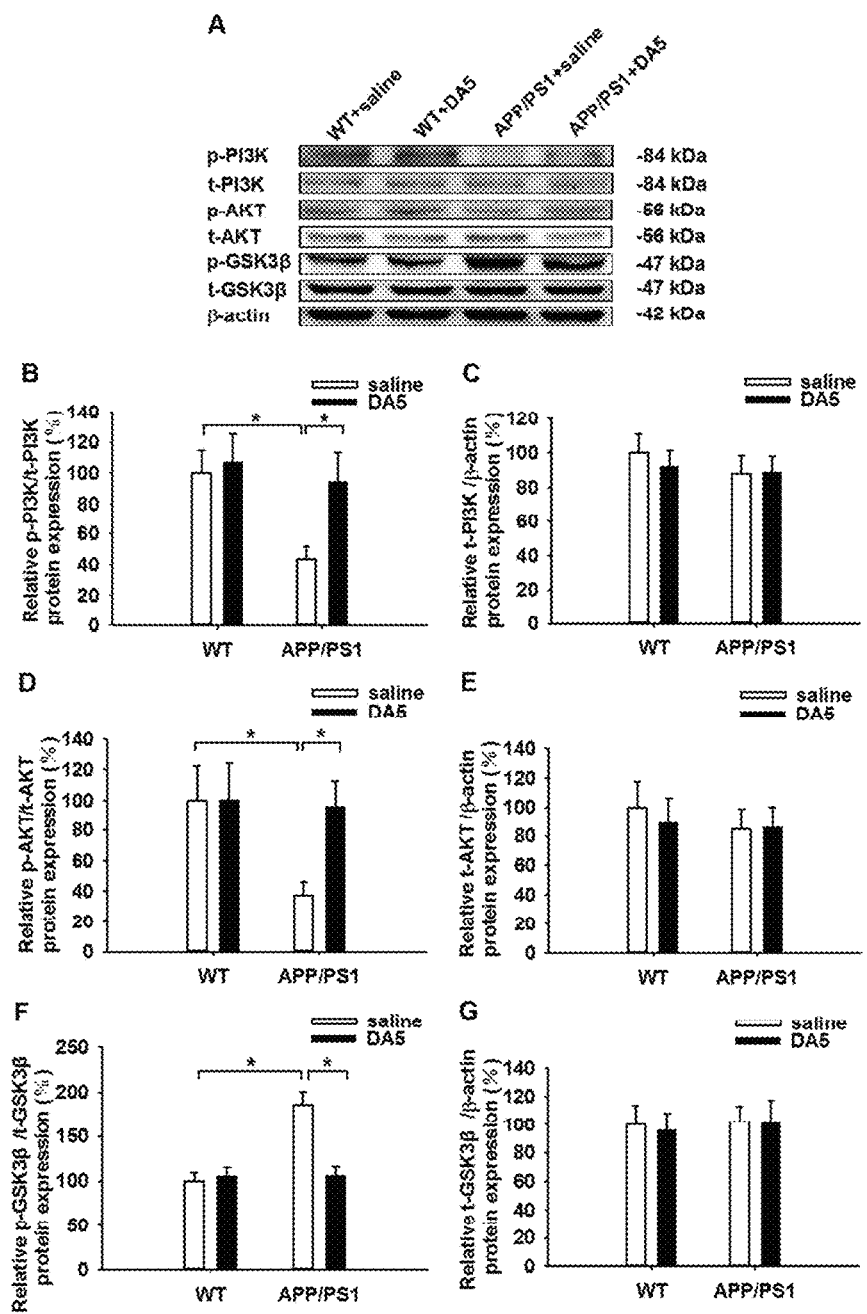

FIG. 11 shows a western blot and graphs illustrating DA5 can protect cognitive behaviours and improve pathological changes in AD mice. Treatment of APP/PS1 mice with DA5 prevents excessive activation of GSKβ by upregulating P13/AKT signalling (a-g). *=p<0.05, N=6 per group.

FIG. 12 details amino acid sequences of peptides as described herein.

DETAILED DESCRIPTION OF EMBODIMENTS OF THE INVENTION

The practice of embodiments of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, $2_{nd}$ ed., 2002, CRC Press; The Dictionary of Cell and Molecular Biology, $3^{rd}$ ed., Academic Press; and the Oxford University Press, provide a person skilled in the art with a general dictionary of many of the terms used in this disclosure.

The present disclosure relates to the use of GIP/GLP-1 co-agonist peptides. The native human GLP-1 peptide and GIP peptide sequences are known in the art. The term "GLP-1", or "hGLP-1" as used herein refers to the human Glucagon-Like Peptide-1 (GLP-1 (7-37)), the sequence of which is included herein as SEQ ID. No. 13.

The peptide having the sequence of SEQ ID. No 13 may also be designated "native" GLP-1.

The *Homo sapiens* GLP-1(7-37) sequence is:

```
                                         (SEQ ID No. 13)
HAEGTFTSDV SSYLEGQAAK EFIAWLVKGR G-OH.
```

The term "GIP", or "hGIP" as used herein refers to the human Gastric Inhibitory Peptide (also known as glucose-dependent insulinotropic peptide) the sequence of which is included herein as SEQ. ID. No. 14. The peptide having the sequence of SEQ. ID. No. 14 may also be designated "native" GIP:

```
                                         (SEQ ID. No 14)
YAEGTFISDYSIAMDKIHQQDFVNWLLAQKGKKNDWKHNITQ-OH.
```

As used herein, a general reference to "GIP" or "GLP-1" in the absence of any further designation is intended to mean native GIP or native GLP-1, respectively.

As used herein, the term "peptide" encompasses a sequence of 3 or more amino acids and typically less than 50 amino acids, wherein the amino acids are naturally occurring or non-naturally occurring amino acids. Non-naturally occurring amino acids refer to amino acids that do not naturally occur in vivo but which, nevertheless, can be incorporated into the peptide structures described herein.

As used herein, the terms "polypeptide" and "protein" are terms that are used interchangeably to refer to a polymer of amino acids, without regard to the length of the polymer. Typically, polypeptides and proteins have a polymer length that is greater than that of "peptides".

As used herein an amino acid "modification" refers to a substitution, addition or deletion of an amino acid, and includes substitution with or addition of any of the 20 amino acids commonly found in human proteins, as well as atypical or non-naturally occurring amino acids. Throughout the application, all references to a particular amino acid position by number (e.g. position 28) refer to the amino acid at that position in the GIP/GLP-1 dual agonist of embodiments of the present invention.

Throughout this specification, the conventional one letter and three letter codes for naturally occurring amino acids are used, as well as generally accepted three letter codes for other amino acids, such as for example Aib (α-aminoisobutyric acid).

Thus, in an aspect of the present invention, there is provided a GIP/GLP-1 co-agonist peptide, or a derivative or a pharmaceutically acceptable salt or solvate of the peptide or the derivative, for use in the treatment and/or prophylaxis of a neurological disorder. Aptly, the co-agonist peptide has a GLP-1 percentage potency within about 10-fold of the GIP percentage potency.

As used herein, the term "agonist" refers to a substance (ligand) that activates the receptor type in question. The terms "dual agonist" and "co-agonist" are used herein are interchangeable and refer to a substance (ligand) that activate two receptor types. Aptly, the GIP/GLP-1 co-agonist peptides described herein have balanced activity at both the GLP-1R and the GIPR. In one embodiment, the co-agonist peptide has an $EC_{50}$ at the human GLP-1 receptor within about 10-fold of the $EC_{50}$ at the human GIP receptor. Activity in in vitro assays may be used as a measure of the peptides' activity.

Aptly, the peptides described herein are synthesized by means of solid-phase or liquid-phase peptide synthesis, as described in for example WO98/11125. Aptly, the peptides may be synthesized as described in Finan et al. (*Sci. Transl. Med.* 5 209ra151 (2013) pp 1 to 16).

The peptides of the present disclosure may be formulated as pharmaceutical compositions prepared for storage or administration for use in the treatment and/or prevention of a neurological disorder as described herein. Such a composition typically comprises a therapeutically effective amount of a GIP/GLP-1 co-agonist peptide, in the appropriate form, in a pharmaceutically acceptable carrier.

The therapeutically effective amount of a GIP/GLP-1 co-agonist peptide as described herein will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The peptides of the present disclosure may be particularly useful for treatment of humans.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the person skilled in the art.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, arginine, lysine, or acetate or mixtures thereof. The term further encompasses any agents listed in the US Pharmacopeia for use in animals, including humans.

The term "pharmaceutically acceptable salt" refers to a salt of any one of the GIP/GLP-1 co-agonist peptide of embodiments of the invention. Salts include pharmaceutically acceptable salts such as acid addition salts and basic salts. Examples of acid addition salts include hydrochloride salts, citrate salts and acetate salts. Examples of basis salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", $17^{th}$ edition. Ed. Alfonoso R. Gennaro (Ed.), Mark Publishing Company, Easton, Pa., U.S.A., 1985 and more recent editions, and in the Encyclopaedia of Pharmaceutical Technology.

The term "solvate" in the context of the present disclosure refers to a complex of defined stoichiometry formed between a solute (e.g., a peptide or pharmaceutically acceptable salt thereof according to the present disclosure) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

"Treatment" is an approach for obtaining beneficial or desired clinical results. For the purposes of the present disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions for use in the treatment of a neurological disorder can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, and transdermal) administration. The formulations may conveniently be presented in unit dosage form and may be prepared by any of the methods well known in the art of pharmacy.

As used herein an "effective" amount or a "therapeutically effective amount" of a peptide refers to a nontoxic but sufficient amount of the peptide to provide the desired effect. The amount that is "effective" will vary from subject to subject, depending on the age and general condition of the individual, mode of administration, and the like. An appropriate "effective" amount in any individual case may be determined by one of ordinary skill in the art using routine experimentation.

The terms "patient", "subject" and "individual" may be used interchangeably and refer to either a human or non-human mammal. Aptly, the subject is a human.

The peptides described herein may be used to treat and/or prevent a neurological disorder e.g. a neurodegenerative disorder. In one embodiment, the peptide is for use in the treatment and/or prevention of Alzheimer's disease. Alzheimer's disease (AD) is a neurodegenerative disorder that results in the loss of cortical neurons, especially in the associative neocortex and hippocampus which in turn leads to slow and progressive loss of cognitive functions, ultimately leading to dementia and death. Major hallmarks of the disease are aggregation and deposition of misfolded proteins such as aggregated beta-amyloid peptide as extracellular senile or neuritic 'plaques', and hyperphosphorylated tau protein as intracellular neurofibrillary 'tangles' (NFTs).

Genetically, AD is divided into two forms: (1) early-onset familial AD (<60 years), and (2) late-onset sporadic AD (>60 years). Rare, disease causing mutations in Amyloid precursor protein (APP), Presenilin 1 (PSEN1), and Presenilin 2 (PSEN2) genes are known to result in early-onset familial AD while, APOE (allele 4) is the single most important risk factor for late-onset AD.

Although Alzheimer's disease develops differently for every individual, there are many common symptoms. Early symptoms are often mistakenly thought to be 'age-related' concerns, or manifestations of stress. In the early stages, the most common symptom is difficulty in remembering recent events. When AD is suspected, the diagnosis is usually confirmed with tests that evaluate behaviour and thinking abilities, often followed by a brain scan if available, however, examination of brain tissue is required for a definitive diagnosis.

As the disease advances, symptoms can include confusion, irritability, aggression, mood swings, trouble with language, and long-term memory loss. As the sufferer declines they often withdraw from family and society. Gradually, bodily functions are lost, ultimately leading to death. Since the disease is different for each individual, predicting how it will affect the person is difficult. AD develops for an unknown and variable amount of time before becoming fully apparent, and it can progress undiagnosed for years. On average, the life expectancy following diagnosis is approximately seven years. Fewer than three percent of individuals live more than fourteen years after diagnosis.

In one embodiment, the co-agonist peptide is for use in treating Alzheimer's disease. The peptide may be used to slow down and/or halt the progression of Alzheimer's disease in a subject. The peptide may be for use to slow down and/or prevent the progression to clinical Alzheimer's disease of a subject suffering from pre-clinical Alzheimer's Disease.

In one embodiment, the co-agonist peptide is for use in the treatment and/or prevention of Parkinson's disease. Parkinson's disease is a neurodegenerative disorder characterized by progressive neuronal loss, in particular of dopaminergic neurons of the substantia nigra, leading to motor disturbances such as tremor, rigidity, slowness of movement, and postural instability. In one embodiment, the peptide is for use to reduce and/or prevent motor disturbances associated with Parkinson's disease.

In addition, there is an increasing number of atypical Parkinson syndromes and subclasses of Parkinson's disease, which are associated with learning and memory deficits. Typical examples are Parkinson's Disease Dementia (PDD), Lewy Body Dementia (LBD) and Multi-Systems Atrophy (MSA). The peptide may be for use in the retrieval or improvement of learning processes or learning deficits and/or the prevention, retrieval or improvement of memory loss or memory impairment in a subject suffering from Parkinson's disease.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any embodiments disclosed herein. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Units, prefixes and symbols are denoted in their Système international d'unités (SI) accepted form. Numeric ranges are inclusive of the numbers defining the range. Unless other indicated, amino acid sequences are written left to right in amino to carboxy orientation. All amino acid residues in peptides of embodiments of the invention are preferably of the L-configuration. However, D-configuration amino acids may also be present.

EXAMPLES

Molecular Structures
Peptide Synthesis

Peptides were synthesized by GL Biochem Ltd. (Shanghai). The purity of the peptide was analysed by reversed-phase HPLC and characterised using matrix assisted laser desorption/ionisation time of flight (MALDI-TOF) mass spectrometry, with a purity >99%.

Peptides were reconstituted in Ultrapure® water to a concentration of 1 mg/ml in polypropylene tubes and frozen in aliquots to permit fresh preparation of doses required for injection.

The peptides tested were:
1. Liraglutide (GLP-1 analogue)—

Liraglutide is a peptide drug which is typically administered parenterally. Liraglutide is authorised for the treatment of Type 2 diabetes. Liraglutide is disclosed in WO98/08871 A1, Example 37. The amino acid sequence of liraglutide is shown in SEQ ID. No. 15.

The fatty acid is linked to amino acid Lys at position 26. The amino acid Lys at position 34 has been replaced by amino acid Arg.

2. DAla$^2$GIP-Lys$^{37}$-γ-Glu-PAL (GIP analogue)
   The sequence of DAla$^2$GIP-Lys$^{37}$-γ-Glu-PAL is:

Yd-AEGTFISDYSIAMDKIHQQDFVNWLLAQKGKK(γ-E-C16)NDWK
HNITQ

Liraglutide is a GLP-1 receptor mono agonist, whilst DAla$^2$GIP-Lys$^{37}$-γ-Glu-PAL is a GIP receptor mono agonist.

3. A peptide referred to herein as DA4 which has the following amino acid sequence:

YXEGTFTSDYSIYLDKQAAXEFVNWLLAGGPSSGAPPPSKKKKKK-NH2

X=amino-isobutyric acid
The DA4 peptide is a GLP-1/GIP dual agonist.

4. A peptide referred to herein as DA5 which has the following amino acid sequence:

YXEGTFTSDYSIYLDKQAAXEFVNWLLAGGPSSGAPPPSKRRQRRKKR
GY-NH2

X=amino-isobutyric acid
The DA5 peptide is a GLP-1/GIP dual agonist.

Example 1

Transgenic Alzheimer's Disease Mouse Model

Animal models have been developed to test novel drugs. A standard model for Alzheimer's disease is transgenic mice that express human mutated genes for amyloid production that are known to induce Alzheimer's disease in humans. These APP/PS1 transgenic mice recapitulate some of the symptoms of Alzheimer's disease such as the aggregation of amyloid in the brain, memory loss and the loss of synapses (Radde et al., 2006).

The APP/PS1 mice express human Swedish mutated APP and human mutated presenilin-1 which induce Alzheimer's Disease in humans.

The dose of peptide tested was 10 nmol/kg body weight. The peptides were administered by a once-daily intraperitoneal injection for 8 weeks. Saline injections were administered as a control. Six animals per group were injected with a peptide or a saline control.

Brain Tissue Analysis for Amyloid Plaques and Synapse Numbers in AD Mice

Animals (6 per group) were perfused transcardially with 30 ml of ice-cold PBS and 30 ml of ice-cold 4% paraformaldehyde to postfix the brain. The brains were removed and placed in fresh 30% sucrose solution in PBS to cryoprotect tissue and cut at a thickness of 40 μm on a cryostat. Sections were chosen according to stereological rules, with the first section taken at random and every 5th section afterwards. Between 7 and 13 sections were analysed per brain.

Immunostaining techniques were used to assess the neuronal plaque load (anti beta-amyloid rabbit polyclonal antibody (1:200, rabbit polyclonal-Invitrogen 71-5800) and of synaptophysin (polyclonal rabbit anti-synaptophysin primary antibody, 1:2000, Abcam, Cambridge, UK) to measure the amount of synapses in the cortex. Brain samples were first exposed to 99% formic acid for 7 minutes and then washed 3 times for 10 minutes in TBS. Pre-treatment with 99% formic acid is known to drastically increase the detection of beta-Amyloid in formalin-fixed brain samples. Then samples were incubated in 0.3% H2O2 (Sigma Aldrich;

Cat.-No.: 516813) in TBS for 30 minutes on the shaker to deplete endogenous peroxides activity, and were 3 times washed in TBS for 10 minutes afterwards.

To increase permeability of membranes in the brain tissue, samples were exposed to 0.3% Triton X-100 (Sigma Aldrich; Cat.-No.: 516813) in TBS for 10 minutes on the shaker. Unspecific proteinophilic binding in the tissue was saturated by incubating the samples with 5% goat serum (Gibco; Cat.-No.: 16210-064) in TBS for 30 minutes on the shaker.

A primary antibody against beta-Amyloid or synaptophysin was added and incubated overnight on the shaker at 4° C. The antibody was polyclonal and raised against a synthetic beta-Amyloid 1-43 peptide in rabbit. The primary antibody was used in a final dilution of 1 to 250 in TBS containing 2% goat serum and 10% Triton X-100. Afterwards, the samples were washed with TBS 3 times for 10 minutes and a secondary antibody was added for 90 minutes on the shaker at 4° C. The secondary antibody was a biotinylated anti-rabbit IgG raised in goat (Vectastain ABC Kit, Rabbit IgG; Vector Laboratories; Cat.-No.: PK-6101), and was used in a final dilution of 1 to 60 in TBS containing 1% goat serum and 10% Triton-X-100.

After washing 3 times for 10 minutes in TBS, samples were incubated in TBS containing 3% avidin solution (Vectastain ABC Kit, Rabbit IgG; Vector Laboratories; Cat.-No.: PK-6101) and 3% biotinylated horseradish peroxidase solution (Vectastain ABC Kit, Rabbit IgG; Vector Laboratories; Cat.-No.: PK-6101) for 90 minutes at 4° C. on the shaker. The samples were then washed 3 times in TBS for 10 minutes and then stained by adding phosphate-buffered saline containing 3% SG blue solution (SG Blue Peroxidase Kit; Vector Laboratories; Cat.-No.: SK-4700) and 3% H2O2 solution for 5 minutes and then again washed 3 times for 10 minutes with phosphate-buffered saline.

To enhance staining, samples were incubated with ddH2O containing 0.5% CuSO4 (w/w) for 5 minutes. After washing 3 times for 10 minutes in ddH2O, the brain slices were put onto silane-coated glass slides with a fine brush where they could dry overnight. Finally the slides were cover slipped with an aquatic mounting medium (VectaMountAQ Mounting Medium; Vector Laboratories, Cat.-No.: H-5501). As control served a set of samples from a 17 month old non-transgenic littermate processed together with the experimental samples.

Sections photographed under a microscope (Zeiss, Germany), randomised unbiased dissectors were overlain on to the brain section images and analysed using a Multi threshold plug-in with the software Image J (NIH, USA). Data were analysed using a one-way ANOVA with post-hoc Bonferroni tests.

Parkinson Mouse Model

A standard model to induce Parkinson like symptoms in mice is the injection of the chemical (MPTP) (Li et al., 2009). This chemical impairs or kills neurons in the brain that produce dopamine. The mice develop motor impairments, and the dopaminergic neurons in the brain are reduced in numbers and function. The enzyme tyrosine hydroxylase (TH) is required to synthesise dopamine. A loss of TH signifies a loss of dopamine production (Harkavyi et al., 2008).

Adult male C57BL/6 mice were given the dopaminergic toxin MPTP (20 mg/kg in 0.1 mL of PBS i.p. at 2-h intervals of 4 doses MPTP; Sigma) or vehicle (PBS) for one day. This treatment selectively affects dopaminergic neurons and induces Parkinson-like symptoms in mice. One group did not receive MPTP as a non-lesioned control.

The dose of peptide tested was 10 nmol/kg body weight. The peptides were administered by a once-daily intraperitoneal injection for 2 weeks. Saline injections were administered as a control. Six animals per group were injected with a peptide or a saline control.

Rotarod Motor Control Test

The rotarod consists of a rotating pole that accelerates over time. Mice are placed on the rod, and motor skills are tested by accelerating the rotation. As the rotation increases, animals lose grip and fall on a cushion located below the rod. Mice were given three trials with 45 min inter-trial intervals on each of 2 consecutive days for 3 weeks. Each animal's endurance time was recorded, and the average was calculated. Data were analysed using a one-way ANOVA with post-hoc Bonferroni tests.

Immunohistochemistry for TH in the Substantia Nigra Pars Compacta and the Striatum Six animals per group were analysed for expression of tyrosine hydroxylase (TH), a marker for dopamine production. Coronal brain sections (20 µm) from striatum (bregma 11 to 10.2) and SNpc (bregma 24.80 to 26.04) were analysed by immunohistochemistry using antibodies recognising TH.

Sections were cut on a cryostat and postfixed in 4% paraformaldehyde, washed in PBS, treated with 0.3% H2O2 in methanol for 20 min, and washed again. Incubation with TH (1:800) antibody was at 48° C. overnight in PBS with 0.1% Tween and 10% goat serum. Sections were incubated for 1 hr at room temperature with biotinylated secondary antibody diluted in 0.1% PBS-Tween. DAB staining was performed according to the Vectastain ABC kit instructions (Vector Laboratories). For each animal, three tissue sections from one level of striatum were stained and analysed for TH-positive fibre innervation. To achieve a TH cell count representative of the whole SN, each animal was analysed at four and three rostrocaudal levels (bregma −4.80 to −6.04). Two tissue sections from each level were quantified by immunohistochemistry.

Data were analysed using a one-way ANOVA with post-hoc Bonferroni tests. The results are illustrated in FIGS. 1 to 4.

Conclusion

The results demonstrate that both GLP-1/GIP dual agonist peptides (DA4 and DA5) showed superior neuroprotection over single GLP-1 and GIP analogues in animal models of Alzheimer's and Parkinson's disease. Thus, the data of the present examples demonstrate that both peptides DA4 and DA5 may be considered suitable for use in the treatment and/or prevention of neurodegenerative disorders such as, for example, Alzheimer's Disease and/or Parkinson's Disease.

Example 2

Materials and methods in Example 2 are the same as Example 1 except when stated. Reagents used in Example 2 only include antibodies to p-PI3Kp85, PI3Kp85, p-Akt (ser473), Akt, p-GSK3β (Y216), and GSK3β from Abcam, Inc. Cambridge, UK. The antibody to p-tau (AT8) from Thermo Scientific USA. Mouse Anti-β-actin, Anti-Rabbit IgG, Anti-mouse IgG, CY3-Anti-mouse IgG, RIPA Lysate, BCA Protein Assay Kit, DAPI staining solution and Anti-fluorescence decay agent from Boster (Wuhan, China).

Open Field Test for Investigating Locomotor Activity and Exploratory Behaviour.

Before the experiment, the animals had a 30 min of adaptation in the laboratory. The open field was divided into 16 equal size squares with defining 4 squares in the middle as central area and the rest as peripheral area. Each mouse was placed individually in the apparatus (40 cm×40 cm×40 cm) from the center for 5 min and the total distance as well as the percentage of time in center were recorded by Smart 3.0 software system (Panlab, Spain) at the same time. The apparatus was cleaned with 70% ethanol before each test.

Y-Maze Test for Measuring the Working Memory in AD Mice

Spatial working memory was assessed by recording spontaneous alternation behaviour in a Y-maze. The maze was made of three 30 cm long, 7 cm high, 15 cm wide arms and the arms converged in an equilateral triangular central area. Each mouse was placed at the central triangular area and allowed to move freely through the maze during an 8-min session. The total arm entries and arm order was recorded by Smart 3.0 software system. Alternation was defined as successive entries into the three arms, on overlapping triplet sets. The percent alternation was calculated as the ratio of actual to possible alternations (defined as the total number of arm entries minus 2) multiplied by 100.

Classical Morris Water Maze and Reversal Morris Water Maze Tests for Measuring Spatial Learning and Memory.

Classical Morris water maze (MWM) test was used to investigate spatial reference memory of mouse. The water maze mainly included a stainless steel pool and a platform in the pool for escape. There were several landmarks fixed to the walls of the water maze. The pool was filled with tap water at 22±2° C. The first phase was acquisition trial phase which was consisted of five training days (days 1-5) and four trials each day. The pool (diameter, 120 cm; high, 50 cm) was divided into four quadrants and the escape platform (diameter, 12 cm) hidden 1 cm beneath the water surface was placed in the center of the first quadrant. Four points equally spaced along the circumference of the pool were served as the starting position, which was chosen randomly across the four trials per day. When the mouse climbed onto the platform or the time reached 1 minute, the records stopped. The escape latencies were recorded by Ethovision 3.0 software system (Noldus Information Technology, the Netherlands). The second phase was probe trial phase. On the day after finishing the acquisition task (day 6), a probe trial was performed to assess the spatial memory. The platform was removed from the pool, and animals were allowed to swim freely for 1 min. The percentage of swimming time in target quadrant (the first quadrant) and frequency of platform crossing were recorded. Reversal MWM test was used to observe the ability of mice to relearn and cognitive flexibility. After classical MWM test, the platform was moved to reversal quadrant (the third quadrant), and mice were placed into the water for similar four days' acquisition trial and one day' probe trial as mentioned above. The third phase was visible platform test. Raise the platform 1 cm above the water level and the mice were placed in two randomly selected quadrants. Swimming time to target was recorded.

In Vivo Hippocampal Measurements of L-LTP in AD Mice

Mice were anesthetized with urethane (Sigma, UK, 1.5 g/kg, i.p.) and placed in a stereotaxic apparatus (RWD Life Science, China) for L-LTP recording. Cut off the scalp and expose the skull, small holes were drilled on one side of the skull (2.0 mm posterior to bregma and 1.5 mm lateral to the midline).

A pair of parallel stimulating/recording electrodes (Sequim, Wash., USA) was inserted at the Schaffer collateral and stratum radiatum in the CA1 region of hippocampus. Baseline fEPSPs were elicited by test stimuli at an interval of 30 seconds and 30 minutes fEPSPs were recorded to observe whether the underlying synaptic transmission is affected. Then two paired test stimuli with an interval of 50 ms were given before HFS to induce paired-pulse facilitation (PPF). The change in PPF ratio, calculated by dividing the slope of the second fEPSP by the slope of the first fEPSP, is viewed to be related with the changes in neurotransmitter release from presynaptic terminals. L-LTP was induced by three sets of high-frequency stimulation (HFS) with an interval of 5 minutes. Each set of HFS includes three trains of 20 pulses with 5 ms of interstimulus interval (200 Hz). The fEPSPs were recorded for 180 minutes after HFS. All events were recorded by a biological signal processing system (Chengdu Instruments Ltd, China). The percentage change of fEPSPs in each group after HFS was compared.

Immunostaininq for Phosphorylated Tau Protein in the Hippocampus

After in vivo hippocampal L-LTP recording, the mice were anesthetized with chloral hydrate (0.007 ml/g) by intraperitoneal injection and then the brain tissue was fixed with paraformaldehyde for 24 hours, after that the tissue was transferred to 30% sucrose solution for dehydration. The brain tissue was harvested, frozen in −80° C., and then sliced at a thickness of 30 µm, put the frozen section in PBS, blocked with normal goat serum (Solarbio, Beijing, China), followed by adding the primary antibody, second antibody and DAPI. Phosphorylated tau protein was observed by confocal laser scanning microscopy.

Western Blotting for Assessing Hippocampal Levels of PI3K/AKT/GSK3β

The hippocampi of mouse were dissected and homogenized in tissue protein extraction reagent, and protein concentration was measured using BCA Protein Assay Kit. A total of 50 µg of protein was used from each sample. Sample proteins were separated on 12% SDS-polyacrylamide gels. After that, the proteins were transferred onto PVDF membranes and nonspecific binding was blocked with 5% BSA. A primary antibody was used to incubate the membranes overnight at 4° C., followed by a secondary antibody for 2 h. The optical density of the target strip (p-PI3K, t-PI3K, p-AKT, t-AKT, p-GSK3β and t-GSK3β) was analyzed by using a gel image processing system.

Data were analysed using a one-way ANOVA with post-hoc Bonferroni tests. The results are illustrated in FIGS. 5 to 11.

Conclusion

The results present in this study confirmed the protective effects of the GLP-1/GIP dual agonist DA5 peptide on the cognitive function and pathological characteristics in APP/PS1 transgenic AD mice. The neuroprotection of the DA5 peptide may be associated with the improvement of hippocampal synaptic plasticity and PI3K/AKT/GSK3β signalling pathway. The above results suggest that the DA5 peptide may be useful in the treatment of neurodegenerative disease, and particularly may be beneficial for AD patients, especially those with T2DM or hyperglycemia.

The present disclosure also encompasses the subject matter of the following numbered paragraphs:
1. A GIP/GLP-1 co-agonist peptide represented by the general Formula I:

(I)
(SEQ. ID. No. 1)
Tyr-Aib-Glu-Gly-Thr-Phe-Thr-Ser-Asp-Tyr-Ser-Ile-

Tyr-Leu-Asp-Lys-Gln-Ala-Ala-Aib-Glu-Phe-Val-

Xaa$^{24}$-Trp-Leu-Leu-Ala-Gly-Y1-Y2-R$^2$ wherein Xaa$^{24}$ is selected from Asn and Cys;
Y1 is selected from absent or an extension comprising at least eight amino acid molecules;
Y2 is selected from:

(SEQ. ID. No. 2)
Lys-Lys-Lys-Lys-Lys;

(SEQ. ID. No. 3)
Lys-Lys-Lys-Lys-Lys-Lys (SEQ. ID. No 4)
Arg-Arg-Gln-Arg-Arg-Lys-Lys-Arg-Gly-Tyr;
and (SEQ. ID. No 5)
Lys-Arg-Arg-Gln-Arg-Arg-Lys-Lys-Arg-Gly-Tyr;

R$^2$ is selected from —NH2 or —OH, or a derivative or a pharmaceutically acceptable salt or solvate of the peptide or the derivative.
2. The peptide according to paragraph 1, wherein Y2 is Lys-Lys-Lys-Lys-Lys or Lys-Lys-Lys-Lys-Lys-Lys.
3. The peptide according to paragraph 1, wherein Y2 is Arg-Arg-Gln-Arg-Arg-Lys-Lys-Arg-Gly-Tyr or Lys-Arg-Arg-Gln-Arg-Arg-Lys-Lys-Arg-Gly-Tyr.
4. The peptide according to any preceding paragraph, wherein Xaa$^{24}$ is Cys.
5. The peptide according to any of paragraphs 1 to 3, wherein Xaa$^{24}$ is Asn.
6. The peptide according to any preceding paragraph, wherein Y1 is an extension comprising at least 10 amino acids.
7. The peptide according to any preceding paragraph, wherein Y1 is selected from:

(SEQ. ID. No. 6)
Gly-Pro-Ser-Ser-Gly-Ala-Pro-Pro-Pro-Ser;

(SEQ. ID. No. 7)
Gly-Pro-Ser-Ser-Gly-Ala-Pro-Pro-Pro-Ser-Lys;

(SEQ. ID. No. 8)
Gly-Pro-Ser-Ser-Gly-Ala-Pro-Pro-Pro-Ser-Cys;

(SEQ. ID. No. 9)
Pro-Ser-Ser-Gly-Ala-Pro-Pro-Pro-Ser;

(SEQ. ID. No. 10)
Pro-Ser-Ser-Gly-Ala-Pro-Pro-Ser;

and
absent.
8. The peptide according to paragraph 7, wherein Y1 is Gly-Pro-Ser-Ser-Gly-Ala-Pro-Pro-Pro-Ser.
9. The peptide according to paragraph 7, wherein Y1 is Gly-Pro-Ser-Ser-Gly-Ala-Pro-Pro-Pro-Ser-Cys.
10. The peptide according to paragraph 7, wherein Y1 is Gly-Pro-Ser-Ser-Gly-Ala-Pro-Pro-Pro-Ser-Lys.

11. The peptide according to paragraph 1, which comprises the amino acid sequence of:

(SEQ. ID. No. 11)
YXEGTFTSDYSIYLDKQAAXEFVNWLLAGGPSSGAPPPSKKKKKK-NH2 wherein X=aminoisobutyric acid.
12. The peptide according to paragraph 1, which consists essentially of the amino acid sequence of:

(SEQ. ID. No. 11)
YXEGTFTSDYSIYLDKQAAXEFVNWLLAGGPSSGAPPPSKKKKKK-NH2 wherein X=aminoisobutyric acid.
13. The peptide according to paragraph 1, which comprises the amino acid sequence of:

(SEQ. ID. No. 12)
YXEGTFTSDYSIYLDKQAAXEFVNWLLAGGPSSGAPPPSKRRQRRKKR
GY-NH2 wherein X=aminoisobutyric acid.
14. The peptide according to paragraph 1, which consists essentially of the amino acid sequence of:

(SEQ. ID. No. 12)
YXEGTFTSDYSIYLDKQAAXEFVNWLLAGGPSSGAPPPSKRRQRRKKR
GY-NH2 wherein X=aminoisobutyric acid.
15. The peptide according to any preceding paragraph, which comprises a hydrophilic moiety covalently linked to an amino acid.
16. The peptide according to paragraph 15 which comprises a hydrophilic moiety covalently linked to an amino acid at position 24.
17. The peptide according to paragraph 15, which comprises a hydrophilic moiety covalently linked to an amino acid at position 39 or 40, when Y1 is an extension comprising at least 10 amino acids or at least eleven amino acids.
18. The peptide according to paragraph 17, wherein Xaa$^{39}$ or Xaa$^{40}$ is Cys and wherein the peptide comprises a hydrophilic moiety covalently linked to Cys(39) or Cys(40).
19. The peptide according to paragraph 15, wherein Xaa$^{24}$ is Cys and wherein the peptide comprises a hydrophilic moiety covalently linked to Cys(24).
20. The peptide according to any of paragraphs 15 to 19, wherein the hydrophilic moiety is a water-soluble polymer.
21. The peptide according to paragraph 20, wherein the water-soluble polymer is a polyethylene glycol moiety and optionally is a polyethylene glycol moiety having a molecular weight of between about 20,000 Daltons and about 60,000 Daltons.
22. The peptide according to any preceding paragraph, wherein the peptide is conjugated with a lipophilic substituent.
23. The peptide according to paragraph 22, wherein the lipophilic substituent comprises a hydrocarbon chain having 8 to 24 carbon (C) atoms.
24. The peptide according to paragraph 22 or paragraph 23, wherein the lipophilic substituent comprises an acyl group.
25. The peptide according to paragraph 24, wherein the lipophilic substituent is a fatty acid molecule.
26. The peptide according to paragraph 25, wherein the fatty acid molecule is selected from a C-8 octanoyl group, a C-10 decanoyl group, a C-12 lauroyl group, a C-14 myristoyl group, a C-16 palmitoyl group, a C-18 stearoyl group and a C-20 acyl group.

27. The peptide according to any of paragraphs 22 to 26, wherein the lipophilic substituent is attached to an amino acid at the carboxyl-terminus of the peptide.

28. The peptide according to paragraph 27, wherein the lipophilic substituent is attached to an amino acid at position 40.

29. The peptide according to any of paragraphs 22 to 28, wherein the lipophilic substituent is covalently bonded to a side chain of an amino acid of the peptide.

30. The peptide according to any of paragraphs 22 to 29, which comprises a spacer which conjugates the lipophilic substituent to an amino acid residue.

31. The peptide according to paragraph 30, wherein the spacer is a residue from a naturally occurring or unnatural amino acid, wherein the spacer comprises a residue of Gly, Pro, Ala, Val, Leu, Ile, Met, Cys, Phe, Tyr, Trp, His, Lys, Arg, Gln, Asn, α-Glu, γ-Glu, ε-Lys, Asp, Ser, Thr, Gaba, Aib, β-aminohexonyl, 7-aminoheptanoyl, 8-aminooctanoyl, 9-aminononanoyl, 10-aminodecanoyl or 8-amino-3,6-dioxaoctanoyl.

32. The peptide according to paragraph 31, wherein the spacer is γ-Glu.

33. The peptide according to paragraph 31 or paragraph 32, wherein the spacer is a dipeptide, optionally wherein the spacer comprises two negatively charged amino acids and further optionally wherein the spacer is γ-Glu-γ-Glu.

34. The peptide according to any preceding paragraph, further comprising one or more conservative substitutions.

35. The peptide according to any preceding paragraph, which is for use in the treatment and/or prophylaxis of a neurological disorder.

36. The peptide according to paragraph 35, wherein the peptide is for use in the treatment of a neurological disorder which is caused by or associated with beta-amyloid protein plaque deposition in an area of the patient.

37. The peptide according to paragraph 36, wherein the beta-amyloid plaque deposition is in the brain of the patient.

38. The peptide according to paragraph 35, which is for use in the treatment and/or prophylaxis of a neurological disorder caused by, or associated with, dysfunction of long-term potentiation of synaptic transmission.

39. The peptide according to paragraph 35, which is for use in the treatment and/or prophylaxis of a neurological disorder caused by, or associated with, inflammation.

40. The peptide according to paragraph 35, which is for use in the treatment of a neurological disorder associated with motor impairment.

41. The peptide according to paragraph 35, which is for use in the treatment and/or prophylaxis of a neurological disorder affecting cognitive function, e.g. dementia, stroke, schizophrenia and/or bipolar disorder.

42. The peptide according to paragraph 41, wherein the disorder is cerebral ischemia associated with stroke.

43. The peptide according to paragraph 35, which is for use in the treatment and/or prophylaxis of a disorder selected from post-traumatic stress disorder, epilepsy, Tourette's syndrome, and hallucinations; and dysfunctional cognitive processes, optionally selected from attention, calculation, memory, judgment, insight, learning and reasoning.

44. The peptide according to paragraph 35, which is for use in the treatment and/or prophylaxis of a neurodegenerative disorder e.g. Alzheimer's disease, Parkinson's disease, Amyotrophic Lateral Sclerosis, peripheral neuropathy, Huntington's disease and Creutzfeldt-Jacob disease.

45. The peptide according to paragraph 35, wherein the neurological disorder is multiple sclerosis.

46. The peptide according to paragraph 45, which is for use in the treatment and/or prophylaxis of a neurological disorder selected from clinical or pre-clinical Alzheimer's disease, prodromal Alzheimer's disease, and clinical or pre-clinical amyloid angiopathy (CAA).

47. The peptide according to paragraph 46, which is for use in the treatment and/or prophylaxis of clinical Alzheimer's disease.

48. The peptide according to paragraph 46, which is for use in the treatment and/or prophylaxis of Parkinson's disease.

49. A method of treating and/or preventing a neurological disorder comprising administering to a patient in need thereof a pharmaceutical composition comprising a GIP/GLP-1 co-agonist peptide, or a derivative or a pharmaceutically acceptable salt or solvate of the peptide or the derivative, wherein said co-agonist peptide is represented by the general Formula I:

(I)
(SEQ. ID. No. 1)
Tyr-Aib-Glu-Gly-Thr-Phe-Thr-Ser-Asp-Tyr-Ser-Ile-

Tyr-Leu-Asp-Lys-Gln-Ala-Ala-Aib-Glu-Phe-Val-Xaa$^{24}$-

Trp-Leu-Leu-Ala-Gly-Y1-Y2-R$^2$ wherein Xaa$^{24}$ is selected from Asn and Cys;
Y1 is selected from absent or an extension comprising at least eight amino acid molecules;
Y2 is selected from:

(SEQ. ID. No 2)
Lys-Lys-Lys-Lys-Lys;

(SEQ. ID. No. 3)
Lys-Lys-Lys-Lys-Lys-Lys (SEQ. ID. No 4)
Arg-Arg-Gln-Arg-Arg-Lys-Lys-Arg-Gly-Tyr;
and (SEQ. ID. No 5)
Lys-Arg-Arg-Gln-Arg-Arg-Lys-Lys-Arg-Gly-Tyr;

R$^2$ is selected from —NH2 or —OH,
or a derivative or a pharmaceutically acceptable salt or solvate of the peptide or the derivative.

50. The method according to paragraph 49, wherein the peptide is as claimed in any of claims 1 to 34.

51. The method according to paragraph 49 or paragraph 50, wherein the neurological disorder is selected from post-traumatic stress disorder, epilepsy, Tourette's syndrome, and hallucinations; and dysfunctional cognitive processes, optionally selected from attention, calculation, memory, judgment, insight, learning and reasoning.

52. The method according to paragraph 49 or paragraph 50, wherein the neurological disorder is a neurodegenerative disorder.

53. The method according to paragraph 52, wherein the neurodegenerative disorder is selected from Alzheimer's Disease, Parkinson's Disease, Huntington's disease, Amyotrophic Lateral Sclerosis, peripheral neuropathy, and Creutzfeldt-Jacob disease.

54. The method according to paragraph 53, wherein the neurological disorder is a neurological disorder selected from clinical or pre-clinical Alzheimer's disease, prodromal Alzheimers disease, and clinical or preclinical amyloid angiopathy (CAA).

55. The method according to paragraph 54, wherein the neurological disorder is clinical Alzheimer's Disease.

56. A peptide for use in the treatment and/or prophylaxis of clinical Alzheimer's Disease, the peptide consisting of the following sequence:

YXEGTFTSDYSIYLDKQAAXEFVNWLLAGGPSSGAPPPSKKKKKK-NH2 wherein X=aminoisobutyric acid.

57. A peptide for use in the treatment and/or prophylaxis of clinical Alzheimer's Disease, the peptide consisting of the following sequence:

YXEGTFTSDYSIYLDKQAAXEFVNWLLAGGPSSGAPPPSKRRQRRKKRG Y-NH2 wherein X=aminoisobutyric acid.

REFERENCES

Aviles-Olmos I, Dickson J, Kefalopoulou Z, Djamshidian A, Ell P, Soderlund T, Whitton P, Wyse R, Isaacs T, Lees A, Limousin P, Foltynie T (2013) Exenatide and the treatment of patients with Parkinson's disease. The Journal of clinical investigation 123:2730-6.

Aviles-Olmos I, Dickson J, Kefalopoulou Z, Djamshidian A, Kahan J, Fmedsci P E, Whitton P, Wyse R, Isaacs T, Lees A, Limousin P, Foltynie T (2014) Motor and Cognitive Advantages Persist 12 Months After Exenatide Exposure in Parkinson's Disease. Journal of Parkinson's disease 4:337-344.

Baggio L L, Drucker D J (2007) Biology of incretins: GLP-1 and GIP. Gastroenterology 132:2131-2157.

Bertilsson G, Patrone C, Zachrisson O, Andersson A, Dannaeus K, Heidrich J, Kortesmaa J, Mercer A, Nielsen E, Ronnholm H, Wikstrom L (2008) Peptide hormone exendin-4 stimulates subventricular zone neurogenesis in the adult rodent brain and induces recovery in an animal model of Parkinson's disease. Journal of neuroscience research 86:326-338.

Blennow K, de Leon M J, Zetterberg H (2006) Alzheimer's disease. Lancet 368:387-403.

Bliss T V P, Collingridge G L (1993) A synaptic model of memory: long-term potentiation in the hippocampus. Nature 361:31-39.

Bomfim T R, Forny-Germano L, Sathler L B, Brito-Moreira J, Houzel J C, Decker H, Silverman M A, Kazi H, Melo H M, McClean P L, Holscher C, Arnold S E, Talbot K, Klein W L, Munoz D P, Ferreira S T, De Felice F G (2012) An anti-diabetes agent protects the mouse brain from defective insulin signaling caused by Alzheimer's disease-associated Abeta oligomers. The Journal of clinical investigation 122:1339-53.

Campbell J E, Drucker D J (2013) Pharmacology, physiology, and mechanisms of incretin hormone action. Cell metabolism 17:819-837.

Cereda E, Barichella M, Cassani E, Caccialanza R, Pezzoli G (2012) Clinical features of Parkinson disease when onset of diabetes came first: A case-control study. Neurology 78:1507-1511.

Christensen M, Knop F K, Holst J J, Vilsboll T (2009) Lixisenatide, a novel GLP-1 receptor agonist for the treatment of type 2 diabetes mellitus. IDrugs: the investigational drugs journal 12:503-513.

Cleary J P, Walsh D M, Hofmeister J J, Shankar G M, Kuskowski M A, Selkoe D J, Ashe K H (2005) Natural oligomers of the amyloid-beta protein specifically disrupt cognitive function. Nature neuroscience 8:79-84.

Duffy A M, Holscher C (2013) The incretin analogue D-Ala(2)GIP reduces plaque load, astrogliosis and oxidative stress in an APP/PS1 mouse model of Alzheimer's disease. Neuroscience 228:294-300.

Elkinson S, Keating G M (2013) Lixisenatide: first global approval. Drugs 73:383-391.

Faivre E, Holscher C (2013a) D-Ala2GIP facilitated synaptic plasticity and reduces plaque load in aged wild type mice and in an Alzheimer's disease mouse model. Journal of Alzheimer's disease: JAD 35:267-283.

Faivre E, Holscher C (2013b) Neuroprotective effects of D-Ala2GIP on Alzheimer's disease biomarkers in an APP/PS1 mouse model. Alzheimer's research & therapy 5:20-28.

Faivre E, Gault V A, Thorens B, Holscher C (2011) Glucose-dependent insulinotropic polypeptide receptor knockout mice are impaired in learning, synaptic plasticity, and neurogenesis. J Neurophysiol 105:1574-1580.

Gault V, Holscher C (2008a) GLP-1 agonists facilitate hippocampal LTP and reverse the impairment of LTP induced by beta-amyloid. European journal of pharmacology 587:112-117.

Gault V A, Holscher C (2008b) Protease-resistant glucose-dependent insulinotropic polypeptide agonists facilitate hippocampal LTP and reverse the impairment of LTP induced by beta-amyloid. J Neurophysiol 99:1590-1595.

Gault V A, Flatt P R, O'Harte F P (2003) Glucose-dependent insulinotropic polypeptide analogues and their therapeutic potential for the treatment of obesity-diabetes. Biochemical and biophysical research communications 308:207-213.

Gejl M, Gjedde A, Egefjord L, Møller A, Hansen S B, Vang K, Rodell A B, Braendgaard H, Gottrup H, Schacht A, Møller N, Brock B, Rungby J (2016) In Alzheimer's Disease, Six-Month Treatment with GLP-1 Analogue Prevents Decline of Brain Glucose Metabolism: Randomized, Placebo-Controlled, Double-Blind Clinical Trial. Frontiers in aging neuroscience 8:1-10.

Gengler S, McClean P, McCurtin R, Gault V, Holscher C (2012) Val(8)GLP-1 rescues synaptic plasticity and reduces dense core plaques in APP/PS1 mice. Neurobiology of aging 33:265-276.

Han B, Hu J, Shen J, Gao Y, Lu Y, Wang T (2013) Neuroprotective effect of hydroxysafflor yellow A on 6-hydroxydopamine-induced Parkinson's disease in rats. European journal of pharmacology 714:83-88.

Harkavyi A, Abuirmeileh A, Lever R, Kingsbury A E, Biggs C S, Whitton P S (2008) Glucagon-like peptide 1 receptor stimulation reverses key deficits in distinct rodent models of Parkinson's disease. Journal of neuroinflammation 5:19(11-19).

Holscher C (2014) Insulin, incretins and other growth factors as potential novel treatments for Alzheimer's and Parkinson's diseases. Biochemical Society transactions 42:593-599.

Hunter K, Holscher C (2012) Drugs developed to treat diabetes, liraglutide and lixisenatide, cross the blood brain barrier and enhance neurogenesis. BMC neuroscience 13:33-38.

Irwin N, O'Harte F P, Gault V A, Green B D, Greer B, Harriott P, Bailey C J, Flatt P R (2006) GIP(Lys(16)PAL)

and GIP(Lys(37)PAL): Novel Long-Acting Acylated Analogues of Glucose-Dependent Insulinotropic Polypeptide with Improved Antidiabetic Potential. Journal of medicinal chemistry 49:1047-1054.

Ji C, Xue G F, Lijun C, Feng P, Li D, Li L, Li G, Holscher C (2015) A novel dual GLP-1 and GIP receptor agonist is neuroprotective in the MPTP mouse model of Parkinson's disease by increasing expression of BNDF. Brain research 1634:1-11.

LaFerla F M, Oddo S (2005) Alzheimer's disease: Abeta, tau and synaptic dysfunction. Trends Mol Med 11:170-176.

Li Y, Liu W, Li L, Holscher C (2015) Neuroprotective effects of a GIP analogue in the MPTP Parkinson's disease mouse model. Neuropharmacology 101:255-263.

Li Y, Perry T, Kindy M S, Harvey B K, Tweedie D, Holloway H W, Powers K, Shen H, Egan J M, Sambamurti K, Brossi A, Lahiri D K, Mattson M P, Hoffer B J, Wang Y, Greig N H (2009) GLP-1 receptor stimulation preserves primary cortical and dopaminergic neurons in cellular and rodent models of stroke and Parkinsonism. Proceedings of the National Academy of Sciences of the United States of America 106:1285-1290.

Liu L, Venkatraman S S, Yang Y Y, Guo K, Lu J, He B, Moochhala S, Kan L (2008) Polymeric micelles anchored with TAT for delivery of antibiotics across the blood-brain barrier. Biopolymers 90:617-623.

Liu W, Jalewa J, Sharma M, Li G, Li L, Holscher C (2015) Neuroprotective effects of lixisenatide and liraglutide in the MPTP mouse model of Parkinson's disease. Neuroscience 303:42-50.

Lovshin J A, Drucker D J (2009) Incretin-based therapies for type 2 diabetes mellitus. Nature reviews Endocrinology 5:262-269.

Luchsinger J A, Tang M X, Shea S, Mayeux R (2004) Hyperinsulinemia and risk of Alzheimer disease. Neurology 63:1187-1192.

McClean P, Holscher C (2014) Liraglutide can reverse memory impairment, synaptic loss and reduce plaque load in aged APP/PS1 mice, a model of Alzheimer's disease. Neuropharmacol 76:57-67.

McClean P, Parthsarathy V, Faivre E, Hölscher C (2011) The diabetes drug Liraglutide prevents degenerative processes in a mouse model of Alzheimer's disease. The Journal of neuroscience: the official journal of the Society for Neuroscience 31:6587-6594.

McClean P L, Gault V A, Harriott P, Holscher C (2010) Glucagon-like peptide-1 analogues enhance synaptic plasticity in the brain: A link between diabetes and Alzheimer's disease. European journal of pharmacology 630:158-162.

Moloney A M, Griffin R J, Timmons S, O'Connor R, Ravid R, O'Neill C (2010) Defects in IGF-1 receptor, insulin receptor and IRS-1/2 in Alzheimer's disease indicate possible resistance to IGF-1 and insulin signalling. Neurobiology of aging 31:224-243.

Morris J K, Bomhoff G L, Gorres B K, Davis V A, Kim J, Lee P P, Brooks W M, Gerhardt G A, Geiger P C, Stanford J A (2011) Insulin resistance impairs nigrostriatal dopamine function. Experimental neurology 231:171-180.

Nyberg J, Jacobsson C, Anderson M F, Eriksson P S (2007) Immunohistochemical distribution of glucose-dependent insulinotropic polypeptide in the adult rat brain. Journal of neuroscience research 85:2099-2119.

Ohara T, Doi Y, Ninomiya T, Hirakawa Y, Hata J, Iwaki T, Kanba S, Kiyohara Y (2011) Glucose tolerance status and risk of dementia in the community: The Hisayama Study. Neurology 77:1126-1134.

Radde R, Bolmont T, Kaeser S A, Coomaraswamy J, Lindau D, Stoltze L, Calhoun M E, Jaggi F, Wolburg H, Gengler S, Haass C, Ghetti B, Czech C, Holscher C, Mathews P M, Jucker M (2006) Abeta42-driven cerebral amyloidosis in transgenic mice reveals early and robust pathology. EMBO Rep 7:940-647.

Ristow M (2004) Neurodegenerative disorders associated with diabetes mellitus. J Mol Med 82:510-529.

Scherrmann J M (2002) Drug delivery to brain via the blood-brain barrier. Vascul Pharmacol 38:349-354.

Shen J (2010) Impaired neurotransmitter release in Alzheimer's and Parkinson's diseases. Neuro-degenerative diseases 7:80-83.

Talbot K, Wang H Y, Kazi H, Han L Y, Bakshi K P, Stucky A, Fuino R L, Kawaguchi K R, Samoyedny A J, Wilson R S, Arvanitakis Z, Schneider J A, Wolf B A, Bennett D A, Trojanowski J Q, Arnold S E (2012) Demonstrated brain insulin resistance in Alzheimer's disease patients is associated with IGF-1 resistance, IRS-1 dysregulation, and cognitive decline. The Journal of clinical investigation 122:1316-38.

Windisch M, Gschanes A, Hutter-Paier B (1998) Neurotrophic activities and therapeutic experience with a brain derived peptide preparation. Journal of neural transmission Supplementum 53:289-298.

The invention claimed is:

1. A glucose-dependent insulinotropic peptide/glucagon-like peptide 1 (GIP/GLP-1) co-agonist peptide
which consists of the amino acid sequence of:
YXEGTFTSDYSIYLDKQAAXEFVNWL-LAGGPSSGAPPPSKKKKKK-NH$_2$ (SEQ. ID. No. 11) wherein X=aminoisobutyric acid, or
which consists of the amino acid sequence of:
YXEGTFTSDYSIYLDKQAAXEFVNWL-LAGGPSSGAPPPSKRRQRRKKRGY-NH$_2$ (SEQ. ID. No. 12) wherein X=aminoisobutyric acid.

2. A process for the treatment of a neurological disorder selected from the group consisting of Alzheimer's disease and Parkinson's disease in a subject in need thereof comprising administering to the subject the peptide of claim 1.

3. The process according to claim 2, wherein the neurological disorder is caused by or associated with beta-amyloid protein plaque deposition in an area of the patient.

4. The process according to claim 2, wherein the neurological disorder is caused by, or associated with:

a) dysfunction of long-term potentiation of synaptic transmission; or
b) inflammation.

5. The process according to claim 2, wherein the neurological disorder affects cognitive function.

6. The process according to claim 2, wherein the neurological disorder is a neurodegenerative disorder.

7. The process according to claim 2, wherein the neurological disorder is selected from the group consisting of clinical or pre-clinical Alzheimer's disease, and prodromal Alzheimer's disease.

8. A process for the treatment of clinical Alzheimer's Disease in a subject in need thereof comprising administering to the subject a peptide consisting of the following sequence: (a) YXEGTFTSDYSIYLDKQAAXEFVNWL-LAGGPSSGAPPPSKKKKKK-NH$_2$ wherein X=aminoisobutyric acid (SEQ ID NO: 11); or
(b) YXEGTFTSDYSIYLDKQAAXEFVNWL-LAGGPSSGAPPPSKRRQRRKKRGY-NH$_2$ (SEQ ID NO: 12) wherein X=aminoisobutyric acid.

* * * * *

SEQUENCE LISTING

```
<160> NUMBER OF SEQ ID NOS: 16

<210> SEQ ID NO 1
<211> LENGTH: 31
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2), (20)
<223> OTHER INFORMATION: Xaa = alpha amino-isobutyric acid
<220> FEATURE:
<221> NAME/KEY: VARIANT
<222> LOCATION: (24)
<223> OTHER INFORMATION: Xaa = Cys or Asn
<220> FEATURE:
<221> NAME/KEY: VARIANT
<222> LOCATION: (30)
<223> OTHER INFORMATION: Xaa = absent or an extension comprising at
```

-continued

```
    least eight amino acid molecules
<220> FEATURE:
<221> NAME/KEY: VARIANT
<222> LOCATION: (31)
<223> OTHER INFORMATION: Xaa = extension comprising Lys Lys Lys Lys Lys
      or Lys Lys Lys Lys Lys Lys or Arg Arg Gln Arg Arg Lys Lys Arg Gly
      Tyr or Lys Arg Arg Gln Arg Arg Lys Lys Arg Gly Tyr

<400> SEQUENCE: 1

Tyr Xaa Glu Gly Thr Phe Thr Ser Asp Tyr Ser Ile Tyr Leu Asp Lys
1               5                   10                  15

Gln Ala Ala Xaa Glu Phe Val Xaa Trp Leu Leu Ala Gly Xaa Xaa
            20                  25                  30

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Lys Lys Lys Lys Lys
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic peptide

<400> SEQUENCE: 3

Lys Lys Lys Lys Lys Lys
1               5

<210> SEQ ID NO 4
<211> LENGTH: 10
<212> TYPE: PRT
<213> ORGANISM: Artificial Sequence
<220> FEATURE:
<223> OTHER INFORMATION: synthetic peptide

<400> SEQUENCE: 4

Arg Arg Gln Arg Arg Lys Lys Arg Gly Tyr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Lys Arg Arg Gln Arg Arg Lys Lys Arg Gly Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic peptide

<400> SEQUENCE: 6

Gly Pro Ser Ser Gly Ala Pro Pro Pro Ser
```

<210> SEQ ID NO 7
<211> LENGTH: 11
<212> TYPE: PRT
<213> ORGANISM: Artificial Sequence
<220> FEATURE:
<223> OTHER INFORMATION: synthetic peptide

<400> SEQUENCE: 7

```
Gly Pro Ser Ser Gly Ala Pro Pro Pro Ser Lys
1               5                   10
```

<210> SEQ ID NO 8
<211> LENGTH: 11
<212> TYPE: PRT
<213> ORGANISM: Artificial Sequence
<220> FEATURE:
<223> OTHER INFORMATION: synthetic peptide

<400> SEQUENCE: 8

```
Gly Pro Ser Ser Gly Ala Pro Pro Pro Ser Cys
1               5                   10
```

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

```
Pro Ser Ser Gly Ala Pro Pro Pro Ser
1               5
```

<210> SEQ ID NO 10
<211> LENGTH: 8
<212> TYPE: PRT
<213> ORGANISM: Artificial Sequence
<220> FEATURE:
<223> OTHER INFORMATION: synthetic peptide

<400> SEQUENCE: 10

```
Pro Ser Ser Gly Ala Pro Pro Ser
1               5
```

<210> SEQ ID NO 11
<211> LENGTH: 45
<212> TYPE: PRT
<213> ORGANISM: Artificial Sequence
<220> FEATURE:
<223> OTHER INFORMATION: GIP/GLP-1 co-agonist peptide
<220> FEATURE:
<221> NAME/KEY: VARIANT
<222> LOCATION: (2), (20)
<223> OTHER INFORMATION: Xaa = alpha amino-isobutyric acid

<400> SEQUENCE: 11

```
Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Lys Lys Lys Lys Lys
        35                  40                  45
```

<210> SEQ ID NO 12

```
<211> LENGTH: 50
<212> TYPE: PRT
<213> ORGANISM: Artificial Sequence
<220> FEATURE:
<223> OTHER INFORMATION: GIP/GLP-1 co-agonist peptide
<220> FEATURE:
<221> NAME/KEY: VARIANT
<222> LOCATION: (2), (20)
<223> OTHER INFORMATION: Xaa = alpha amino-isobutyric acid

<400> SEQUENCE: 12

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Arg Arg Gln Arg Arg Lys Lys Arg
        35                  40                  45

Gly Tyr
    50

<210> SEQ ID NO 13
<211> LENGTH: 31
<212> TYPE: PRT
<213> ORGANISM: Artificial Sequence
<220> FEATURE:
<223> OTHER INFORMATION: Human Glucagon-like Peptide 1

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 14
<211> LENGTH: 42
<212> TYPE: PRT
<213> ORGANISM: Artificial Sequence
<220> FEATURE:
<223> OTHER INFORMATION: Human Gastric inhibitory peptide (glucose-
      dependent insulinotropic peptide)

<400> SEQUENCE: 14

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 15
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: VARIANT
<222> LOCATION: (20)
<223> OTHER INFORMATION: Xaa = Lys residue comprising gamma-glutamate
      linker between C16 palmitoyl group and lysine side-chain amino
      group.

<400> SEQUENCE: 15

His Ala Glu Gly Thr Phe Thr Ser Asp Val Ser Ser Tyr Leu Glu Gly
1               5                   10                  15
```

```
Gln Ala Ala Xaa Glu Phe Ile Ala Trp Leu Val Arg Gly Arg Gly
            20                  25                  30

<210> SEQ ID NO 16
<211> LENGTH: 42
<212> TYPE: PRT
<213> ORGANISM: Artificial Sequence
<220> FEATURE:
<223> OTHER INFORMATION: DAla2-GIP-Lys37- y-Glu-PA
<220> FEATURE:
<221> NAME/KEY: VARIANT
<222> LOCATION: (2)
<223> OTHER INFORMATION: Xaa = d-Ala
<220> FEATURE:
<221> NAME/KEY: VARIANT
<222> LOCATION: (33)
<223> OTHER INFORMATION: Xaa = Lys (y-E-C16)

<400> SEQUENCE: 16

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Xaa Asn Asp Trp Lys His Asn Ile Thr Gln
        35                  40
```